US012396894B2

(12) United States Patent
Locke et al.

(10) Patent No.: US 12,396,894 B2
(45) Date of Patent: *Aug. 26, 2025

(54) HYBRID SILICONE AND ACRYLIC ADHESIVE COVER FOR USE WITH WOUND TREATMENT

(71) Applicant: Solventum Intellectual Properties Company, Maplewood, MN (US)

(72) Inventors: Christopher Brian Locke, Bournemouth (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 423 days.

This patent is subject to a terminal disclaimer.

(21) Appl. No.: 17/009,328

(22) Filed: Sep. 1, 2020

(65) Prior Publication Data

US 2020/0397620 A1     Dec. 24, 2020

Related U.S. Application Data

(62) Division of application No. 15/265,718, filed on Sep. 14, 2016, now Pat. No. 10,973,694.

(Continued)

(51) Int. Cl.
*B32B 3/24*     (2006.01)
*A61F 13/02*     (2006.01)
(Continued)

(52) U.S. Cl.
CPC ........ *A61F 13/0223* (2013.01); *A61F 13/023* (2013.01); *A61F 13/025* (2013.01);
(Continued)

(58) Field of Classification Search
CPC ........................ Y10T 428/24339; A61F 13/025
See application file for complete search history.

(56) References Cited

U.S. PATENT DOCUMENTS

| 1,355,846 A | 10/1920 | Rannells |
| 1,944,834 A | 1/1934 | Bennett |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — William P Watkins, III

(57) ABSTRACT

Sealing members and methods of manufacturing the same are described. A first film layer and a second film layer each having a first side and a second side can be provided. A first adhesive can be coupled to the second side of the first film layer to form a first adhesive layer. A second adhesive can be coupled to the second side of the second film layer to form a second adhesive layer, and a third adhesive can be coupled to the first side of the second film layer to form a third adhesive layer. One or more perforations can be formed through the third adhesive layer, the second film layer, and the second adhesive layer. A first side of the third adhesive layer can be coupled to a second side of the first adhesive layer.

35 Claims, 19 Drawing Sheets

Related U.S. Application Data

(60) Provisional application No. 62/220,064, filed on Sep. 17, 2015.

(51) Int. Cl.

| | |
|---|---|
| *A61F 13/0203* | (2024.01) |
| *A61F 13/0246* | (2024.01) |
| *A61F 13/05* | (2024.01) |
| *A61L 15/26* | (2006.01) |
| *A61L 15/58* | (2006.01) |
| *A61M 1/00* | (2006.01) |
| *B32B 5/02* | (2006.01) |
| *B32B 7/12* | (2006.01) |
| *B32B 37/12* | (2006.01) |
| *B32B 38/04* | (2006.01) |
| *B32B 3/26* | (2006.01) |

(52) U.S. Cl.
CPC .......... *A61F 13/0289* (2013.01); *A61F 13/05* (2024.01); *A61L 15/26* (2013.01); *A61L 15/58* (2013.01); *A61M 1/90* (2021.05); *B32B 5/02* (2013.01); *B32B 7/12* (2013.01); *B32B 37/12* (2013.01); *B32B 38/04* (2013.01); *A61L 2420/02* (2013.01); *B32B 3/266* (2013.01); *B32B 2037/1253* (2013.01); *B32B 2038/047* (2013.01); *B32B 2307/726* (2013.01); *B32B 2535/00* (2013.01); *Y10T 428/24331* (2015.01); *Y10T 428/24339* (2015.01)

(56) References Cited

U.S. PATENT DOCUMENTS

| | | | |
|---|---|---|---|
| 2,399,545 A * | 4/1946 | Davis ................... | A61F 13/025 |
| | | | 604/389 |
| 2,547,758 A | 4/1951 | Keeling | |
| 2,552,664 A | 5/1951 | Burdine | |
| 2,632,443 A | 3/1953 | Lesher | |
| 2,682,873 A | 7/1954 | Evans et al. | |
| 2,860,081 A | 11/1958 | Eiken | |
| 2,910,763 A | 11/1959 | Lauterbach | |
| 2,969,057 A | 1/1961 | Simmons | |
| 3,066,672 A | 12/1962 | Crosby, Jr. et al. | |
| 3,122,140 A | 2/1964 | Crowe, Jr. | |
| 3,172,808 A | 3/1965 | Baumann et al. | |
| 3,183,116 A | 5/1965 | Schaar | |
| 3,214,502 A | 10/1965 | Schaar | |
| 3,367,332 A | 2/1968 | Groves | |
| 3,376,868 A | 4/1968 | Mondiadis | |
| 3,515,270 A | 6/1970 | Yang et al. | |
| 3,520,300 A | 7/1970 | Flower, Jr. | |
| 3,568,675 A | 3/1971 | Harvey | |
| 3,645,835 A | 2/1972 | Hodgson | |
| 3,648,692 A | 3/1972 | Wheeler | |
| 3,682,180 A | 8/1972 | McFarlane | |
| 3,742,952 A | 7/1973 | Magers et al. | |
| 3,762,415 A | 10/1973 | Morrison | |
| 3,774,611 A | 11/1973 | Tussey et al. | |
| 3,777,016 A | 12/1973 | Gilbert | |
| 3,779,243 A | 12/1973 | Tussey et al. | |
| 3,811,438 A * | 5/1974 | Economou .......... | A61F 13/0203 |
| | | | 602/55 |
| 3,826,254 A | 7/1974 | Mellor | |
| 3,852,823 A | 12/1974 | Jones | |
| 3,903,882 A | 9/1975 | Augurt | |
| 3,967,624 A | 7/1976 | Milnamow | |
| 3,983,297 A | 9/1976 | Ono et al. | |
| 4,060,081 A | 11/1977 | Yannas et al. | |
| 4,080,970 A | 3/1978 | Miller | |
| 4,096,853 A | 6/1978 | Weigand | |
| 4,139,004 A | 2/1979 | Gonzalez, Jr. | |
| 4,141,361 A | 2/1979 | Snyder | |
| 4,163,822 A | 8/1979 | Walter | |
| 4,165,748 A | 8/1979 | Johnson | |
| 4,174,664 A | 11/1979 | Arnott et al. | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,323,069 A | 4/1982 | Ahr et al. | |
| 4,333,468 A | 6/1982 | Geist | |
| 4,343,848 A | 8/1982 | Leonard, Jr. | |
| 4,360,015 A | 11/1982 | Mayer | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,414,970 A | 11/1983 | Berry | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,529,402 A | 7/1985 | Weilbacher et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,600,146 A | 7/1986 | Ohno | |
| 4,605,399 A | 8/1986 | Weston et al. | |
| 4,608,041 A | 8/1986 | Nielsen | |
| 4,617,021 A | 10/1986 | Leuprecht | |
| 4,640,688 A | 2/1987 | Hauser | |
| 4,655,754 A | 4/1987 | Richmond et al. | |
| 4,664,652 A | 5/1987 | Weilbacher | |
| 4,664,662 A | 5/1987 | Webster | |
| 4,705,543 A | 11/1987 | Kertzman | |
| 4,710,165 A | 12/1987 | McNeil et al. | |
| 4,715,857 A | 12/1987 | Juhasz et al. | |
| 4,733,659 A | 3/1988 | Edenbaum et al. | |
| 4,743,232 A | 5/1988 | Kruger | |
| 4,753,230 A | 6/1988 | Carus et al. | |
| 4,758,220 A | 7/1988 | Sundblom et al. | |
| 4,773,408 A | 9/1988 | Cilento et al. | |
| 4,787,888 A | 11/1988 | Fox | |
| 4,826,494 A | 5/1989 | Richmond et al. | |
| 4,832,008 A | 5/1989 | Gilman | |
| 4,838,883 A | 6/1989 | Matsuura | |
| 4,840,187 A | 6/1989 | Brazier | |
| 4,842,594 A | 6/1989 | Ness | |
| 4,848,364 A | 7/1989 | Bosman | |
| 4,863,449 A | 9/1989 | Therriault et al. | |
| 4,871,611 A | 10/1989 | LeBel | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,930,997 A | 6/1990 | Bennett | |
| 4,935,005 A | 6/1990 | Haines | |
| 4,941,882 A | 7/1990 | Ward et al. | |
| 4,953,565 A | 9/1990 | Tachibana et al. | |
| 4,961,493 A | 10/1990 | Kaihatsu | |
| 4,969,880 A | 11/1990 | Zamierowski | |
| 4,981,474 A | 1/1991 | Bopp et al. | |
| 4,985,019 A | 1/1991 | Michelson | |
| 4,995,382 A | 2/1991 | Lang et al. | |
| 4,996,128 A | 2/1991 | Aldecoa et al. | |
| 5,010,883 A | 4/1991 | Rawlings et al. | |
| 5,018,515 A | 5/1991 | Gilman | |
| 5,025,783 A | 6/1991 | Lamb | |
| 5,028,597 A | 7/1991 | Kodama et al. | |
| 5,037,397 A | 8/1991 | Kalt et al. | |
| 5,042,500 A | 8/1991 | Norlien et al. | |
| 5,086,170 A | 2/1992 | Luheshi et al. | |

(56) References Cited

U.S. PATENT DOCUMENTS

| | | | |
|---|---|---|---|
| 5,092,323 | A | 3/1992 | Riedel et al. |
| 5,092,858 | A | 3/1992 | Benson et al. |
| 5,100,396 | A | 3/1992 | Zamierowski |
| 5,112,323 | A | 5/1992 | Winkler et al. |
| 5,127,601 | A | 7/1992 | Schroeder |
| 5,134,994 | A | 8/1992 | Say |
| 5,149,331 | A | 9/1992 | Ferdman et al. |
| 5,151,314 | A | 9/1992 | Brown |
| 5,152,757 | A | 10/1992 | Eriksson |
| 5,167,613 | A | 12/1992 | Karami et al. |
| 5,176,663 | A | 1/1993 | Svedman et al. |
| 5,180,375 | A | 1/1993 | Feibus |
| 5,215,522 | A | 6/1993 | Page et al. |
| 5,232,453 | A | 8/1993 | Plass et al. |
| 5,244,457 | A | 9/1993 | Karami et al. |
| 5,246,775 | A | 9/1993 | Loscuito |
| 5,261,893 | A | 11/1993 | Zamierowski |
| 5,266,372 | A | 11/1993 | Arakawa et al. |
| 5,270,358 | A | 12/1993 | Asmus |
| 5,271,987 | A | 12/1993 | Iskra |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,329 | A | 8/1994 | Croquevielle |
| 5,342,376 | A | 8/1994 | Ruff |
| 5,344,415 | A | 9/1994 | DeBusk et al. |
| 5,356,386 | A | 10/1994 | Goldberg et al. |
| 5,358,494 | A | 10/1994 | Svedman |
| 5,384,174 | A | 1/1995 | Ward et al. |
| 5,387,207 | A | 2/1995 | Dyer et al. |
| 5,419,769 | A | 5/1995 | Devlin et al. |
| 5,423,778 | A | 6/1995 | Eriksson et al. |
| 5,429,590 | A | 7/1995 | Saito et al. |
| 5,437,622 | A | 8/1995 | Carion |
| 5,437,651 | A | 8/1995 | Todd et al. |
| 5,445,604 | A | 8/1995 | Lang |
| 5,447,492 | A | 9/1995 | Cartmell et al. |
| 5,458,938 | A | 10/1995 | Nygard et al. |
| 5,501,212 | A | 3/1996 | Psaros |
| 5,522,808 | A | 6/1996 | Skalla |
| 5,527,293 | A | 6/1996 | Zamierowski |
| 5,549,584 | A | 8/1996 | Gross |
| 5,549,585 | A | 8/1996 | Maher et al. |
| 5,556,375 | A | 9/1996 | Ewall |
| 5,585,178 | A | 12/1996 | Calhoun et al. |
| 5,599,292 | A | 2/1997 | Yoon |
| 5,607,388 | A | 3/1997 | Ewall |
| 5,611,373 | A | 3/1997 | Ashcraft |
| 5,634,893 | A | 6/1997 | Rishton |
| 5,635,201 | A | 6/1997 | Fabo |
| 5,636,643 | A | 6/1997 | Argenta et al. |
| 5,641,506 | A | 6/1997 | Talke et al. |
| 5,645,081 | A | 7/1997 | Argenta et al. |
| 5,653,224 | A | 8/1997 | Johnson |
| 5,678,564 | A | 10/1997 | Lawrence et al. |
| 5,710,233 | A | 1/1998 | Meckel et al. |
| 5,714,225 | A | 2/1998 | Hansen et al. |
| 5,736,470 | A | 4/1998 | Schneberger et al. |
| 5,759,570 | A | 6/1998 | Arnold |
| 5,776,119 | A | 7/1998 | Bilbo et al. |
| 5,807,295 | A | 9/1998 | Hutcheon et al. |
| 5,830,201 | A | 11/1998 | George et al. |
| 5,878,971 | A | 3/1999 | Minnema |
| 5,902,439 | A | 5/1999 | Pike et al. |
| 5,919,476 | A | 7/1999 | Fischer et al. |
| 5,941,863 | A | 8/1999 | Guidotti et al. |
| 5,964,252 | A | 10/1999 | Simmons et al. |
| 5,981,822 | A | 11/1999 | Addison |
| 5,998,561 | A | 12/1999 | Jada |
| 6,071,267 | A | 6/2000 | Zamierowski |
| 6,083,616 | A | 7/2000 | Dressler |
| 6,086,995 | A | 7/2000 | Smith |
| 6,135,116 | A | 10/2000 | Vogel et al. |
| 6,159,877 | A | 12/2000 | Scholz et al. |
| 6,174,306 | B1 | 1/2001 | Fleischmann |
| 6,191,335 | B1 | 2/2001 | Robinson |
| 6,201,164 | B1 | 3/2001 | Wulff et al. |
| 6,228,485 | B1 | 5/2001 | Leiter |
| 6,238,762 | B1 | 5/2001 | Friedland et al. |
| 6,241,747 | B1 | 6/2001 | Ruff |
| 6,262,329 | B1 | 7/2001 | Brunsveld et al. |
| 6,287,316 | B1 | 9/2001 | Agarwal et al. |
| 6,345,623 | B1 | 2/2002 | Heaton et al. |
| 6,457,200 | B1 | 10/2002 | Tanaka et al. |
| 6,458,109 | B1 | 10/2002 | Henley et al. |
| 6,488,643 | B1 | 12/2002 | Tumey et al. |
| 6,493,568 | B1 | 12/2002 | Bell et al. |
| 6,495,229 | B1 | 12/2002 | Carte et al. |
| 6,503,855 | B1 | 1/2003 | Menzies et al. |
| 6,548,727 | B1 | 4/2003 | Swenson |
| 6,553,998 | B2 | 4/2003 | Heaton et al. |
| 6,566,575 | B1 | 5/2003 | Stickels et al. |
| 6,566,577 | B1 | 5/2003 | Addison et al. |
| 6,626,891 | B2 | 9/2003 | Ohmstede |
| 6,627,215 | B1 | 9/2003 | Dale et al. |
| 6,648,862 | B2 | 11/2003 | Watson |
| 6,680,113 | B1 | 1/2004 | Lucast et al. |
| 6,685,681 | B2 | 2/2004 | Lockwood et al. |
| 6,693,180 | B2 | 2/2004 | Lee et al. |
| 6,695,823 | B1 | 2/2004 | Lina et al. |
| 6,752,794 | B2 | 6/2004 | Lockwood et al. |
| 6,787,682 | B2 | 9/2004 | Gilman |
| 6,806,214 | B2 | 10/2004 | Li et al. |
| 6,814,079 | B2 | 11/2004 | Heaton et al. |
| 6,855,135 | B2 | 2/2005 | Lockwood et al. |
| 6,856,821 | B2 | 2/2005 | Johnson |
| 6,979,324 | B2 | 12/2005 | Bybordi et al. |
| 7,070,584 | B2 | 7/2006 | Johnson et al. |
| 7,154,017 | B2 | 12/2006 | Sigurjonsson et al. |
| 7,402,721 | B2 | 7/2008 | Sigurjonsson et al. |
| 7,569,742 | B2 | 8/2009 | Haggstrom et al. |
| 7,645,269 | B2 | 1/2010 | Zamierowski |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,298,197 | B2 | 10/2012 | Eriksson et al. |
| 8,398,614 | B2 | 3/2013 | Blott et al. |
| 8,449,509 | B2 | 5/2013 | Weston |
| 8,529,532 | B2 | 9/2013 | Pinto et al. |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,632,523 | B2 | 1/2014 | Eriksson et al. |
| 8,679,081 | B2 | 3/2014 | Heagle et al. |
| 8,764,732 | B2 | 7/2014 | Hartwell |
| 8,834,451 | B2 | 9/2014 | Blott et al. |
| 8,920,830 | B2 | 12/2014 | Mathies |
| 8,926,592 | B2 | 1/2015 | Blott et al. |
| 9,017,302 | B2 | 4/2015 | Vitaris et al. |
| 9,192,444 | B2 | 11/2015 | Locke et al. |
| 9,198,801 | B2 | 12/2015 | Weston |
| 9,211,365 | B2 | 12/2015 | Weston |
| 9,289,542 | B2 | 3/2016 | Blott et al. |
| 9,572,719 | B2 | 2/2017 | Long et al. |
| 9,877,873 | B2 | 1/2018 | Coulthard et al. |
| 9,956,120 | B2 | 5/2018 | Locke |
| 10,940,047 | B2 | 3/2021 | Locke et al. |
| 10,946,124 | B2 * | 3/2021 | Locke ............... A61F 13/0269 |
| 11,096,830 | B2 | 8/2021 | Pratt et al. |
| 2001/0030304 | A1 | 10/2001 | Kohda et al. |
| 2001/0051178 | A1 | 12/2001 | Blatchford et al. |
| 2002/0009568 | A1 | 1/2002 | Bries et al. |
| 2002/0016346 | A1 | 2/2002 | Brandt et al. |
| 2002/0065494 | A1 | 5/2002 | Lockwood et al. |
| 2002/0077661 | A1 | 6/2002 | Saadat |
| 2002/0090496 | A1 | 7/2002 | Kim et al. |
| 2002/0115951 | A1 | 8/2002 | Norstrem et al. |
| 2002/0119292 | A1 | 8/2002 | Venkatasanthanam et al. |
| 2002/0120185 | A1 | 8/2002 | Johnson |
| 2002/0130064 | A1 | 9/2002 | Adams et al. |
| 2002/0143286 | A1 | 10/2002 | Tumey |

(56) References Cited

U.S. PATENT DOCUMENTS

| | | |
|---|---|---|
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0070680 A1 | 4/2003 | Smith et al. |
| 2003/0109855 A1 | 6/2003 | Solem et al. |
| 2003/0158577 A1 | 8/2003 | Ginn et al. |
| 2003/0199800 A1 | 10/2003 | Levin |
| 2003/0208175 A1 | 11/2003 | Gross et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2004/0241214 A1 | 12/2004 | Kirkwood et al. |
| 2005/0034731 A1 | 2/2005 | Rousseau et al. |
| 2005/0054998 A1 | 3/2005 | Poccia et al. |
| 2005/0058810 A1 | 3/2005 | Dodge et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2005/0283105 A1 | 12/2005 | Heaton et al. |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1 | 4/2007 | Haggstrom et al. |
| 2007/0135787 A1 | 6/2007 | Raidel et al. |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1 | 1/2008 | Da Silva Macedo |
| 2008/0082059 A1 | 4/2008 | Fink et al. |
| 2008/0090085 A1 | 4/2008 | Kawate et al. |
| 2008/0095979 A1 | 4/2008 | Hatanaka et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0299251 A1 | 12/2009 | Buan |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0030178 A1 | 2/2010 | MacMeccan et al. |
| 2010/0063467 A1 | 3/2010 | Addison et al. |
| 2010/0069863 A1 | 3/2010 | Olson |
| 2010/0106106 A1 | 4/2010 | Heaton et al. |
| 2010/0106118 A1 | 4/2010 | Heaton et al. |
| 2010/0111919 A1 | 5/2010 | Abuzaina et al. |
| 2010/0125259 A1 | 5/2010 | Olson |
| 2010/0159192 A1 | 6/2010 | Cotton |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0191197 A1 | 7/2010 | Braga et al. |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0312159 A1 | 12/2010 | Aali et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0054423 A1 | 3/2011 | Blott et al. |
| 2011/0118683 A1 | 5/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |
| 2011/0237969 A1 | 9/2011 | Eckerbom et al. |
| 2011/0244010 A1 | 10/2011 | Doshi |
| 2011/0257612 A1 | 10/2011 | Locke et al. |
| 2011/0257617 A1 | 10/2011 | Franklin |
| 2011/0280926 A1 | 11/2011 | Junginger |
| 2011/0281084 A1 | 11/2011 | Ashwell |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123359 A1 | 5/2012 | Reed |

(56) References Cited

U.S. PATENT DOCUMENTS

| | | |
|---|---|---|
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Eric Mitchell et al. |
| 2013/0172843 A1 | 7/2013 | Kurata |
| 2013/0189339 A1 | 7/2013 | Vachon |
| 2013/0261585 A1 | 10/2013 | Lee |
| 2013/0296760 A1 | 11/2013 | Ramminger et al. |
| 2013/0304007 A1 | 11/2013 | Toth |
| 2013/0330486 A1 | 12/2013 | Shields |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0249495 A1 | 9/2014 | Mumby et al. |
| 2014/0309574 A1 | 10/2014 | Cotton |
| 2014/0336557 A1 | 11/2014 | Durdag et al. |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0045752 A1 | 2/2015 | Grillitsch et al. |
| 2015/0057625 A1 | 2/2015 | Coulthard |
| 2015/0080788 A1 | 3/2015 | Blott et al. |
| 2015/0080815 A1 | 3/2015 | Chakravarthy et al. |
| 2015/0094646 A1 | 4/2015 | Vinton |
| 2015/0119830 A1 | 4/2015 | Luckemeyer et al. |
| 2015/0119833 A1 | 4/2015 | Coulthard et al. |
| 2015/0119834 A1 | 4/2015 | Locke et al. |
| 2015/0141941 A1 | 5/2015 | Allen et al. |
| 2015/0190286 A1 | 7/2015 | Allen et al. |
| 2015/0209200 A1 | 7/2015 | Fouillet et al. |
| 2015/0217077 A1 | 8/2015 | Scampoli et al. |
| 2015/0290041 A1 | 10/2015 | Richard |
| 2016/0000610 A1 | 1/2016 | Riesinger |
| 2016/0067107 A1 | 3/2016 | Cotton |
| 2016/0144084 A1 | 5/2016 | Collinson et al. |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| DE | 202014100383 U1 | 2/2015 |
| EP | 0059049 A1 | 9/1982 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2195255 A | 4/1988 |
| GB | 2 197 789 A | 6/1988 |
| GB | 2205243 A | 12/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2005205120 A | 8/2005 |
| JP | 2007254515 A | 10/2007 |
| JP | 4129536 B2 | 8/2008 |
| JP | 2012050274 A | 3/2012 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0185249 A1 | 11/2001 |
| WO | 0190465 A2 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004/024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2008149107 A1 | 12/2008 |
| WO | 2009002260 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009124100 A1 | 10/2009 |
| WO | 2009126103 A1 | 10/2009 |

(56) References Cited

FOREIGN PATENT DOCUMENTS

| | | |
|---|---|---|
| WO | 2010011148 A1 | 1/2010 |
| WO | 2010016791 A1 | 2/2010 |
| WO | 2010032728 A1 | 3/2010 |
| WO | 2010056977 A2 | 5/2010 |
| WO | 2010129299 A2 | 11/2010 |
| WO | 2011/008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011135284 A1 | 11/2011 |
| WO | 2011162862 A1 | 12/2011 |
| WO | 2012104584 A1 | 8/2012 |
| WO | 2012112204 A1 | 8/2012 |
| WO | 2012140378 A1 | 10/2012 |
| WO | 2012143665 A1 | 10/2012 |
| WO | 2013009239 A1 | 1/2013 |
| WO | 2013066426 A2 | 5/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014097069 A1 | 6/2014 |
| WO | 2014113253 A1 | 7/2014 |
| WO | 2014/143488 A1 | 9/2014 |
| WO | 2014140608 A1 | 9/2014 |
| WO | 2015065615 A1 | 5/2015 |
| WO | 2015130471 A1 | 9/2015 |
| WO | 2017048866 A1 | 3/2017 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. © Therapy Clinical Guidelines: A Reference Source for Clinicians; Jul. 2007.

Office Action for related U.S. Appl. No. 14/965,675, dated Dec. 12, 2018.

Office Action for related U.S. Appl. No. 14/619,714, dated Dec. 3, 2018.

Office Action for related U.S. Appl. No. 14/630,290, dated Jan. 11, 2019.

Office Action for related U.S. Appl. No. 15/265,718, dated Feb. 7, 2019.

Extended European Search Report for related application 18193559.4, mailed Dec. 17, 2018.

Office Action for related U.S. Appl. No. 14/080,348, dated Apr. 12, 2019.

Japanese Notice of Rejection for related application 2016-570333, dated Feb. 26, 2019.

Office Action for related U.S. Appl. No. 15/410,991, dated May 2, 2019.

Office Action for related U.S. Appl. No. 15/314,426, dated Aug. 29, 2019.

Office Action for related U.S. Appl. No. 15/600,451, dated Nov. 27, 2019.

Australian Office Action for related application 2018278874, dated Feb. 12, 2020.

Office Action for related U.S. Appl. No. 14/630,290, dated Apr. 30, 2020.

Office Action for related U.S. Appl. No. 15/793,044, dated May 13, 2020.

EP Informal Search Report for related application 19186600.3, received May 11, 2020.

Office Action for related U.S. Appl. No. 15/884,198, dated May 19, 2020.

Office Action for related U.S. Appl. No. 16/007,060, dated Aug. 18, 2020.

Office Action for related U.S. Appl. No. 15/937,485, dated Aug. 4, 2020.

Office Action for related U.S. Appl. No. 15/793,044, dated Sep. 24, 2020.

Extended European Search Report for related application 20185730.7, dated Oct. 9, 2020.

Advisory Action for related U.S. Appl. No. 15/793,044, dated Dec. 9, 2020.

Japanese Office Action for related application 2019-235427, dated Jan. 5, 2021.

Office Action for related U.S. Appl. No. 16/151,005, dated Apr. 13, 2021.

Office Action for related U.S. Appl. No. 16/287,862, dated Nov. 2, 2021.

Office Action for related U.S. Appl. No. 16/577,535, dated Mar. 15, 2022.

International Search Report and Written Opinion for PCT/GB2008/003075 mailed Mar. 11, 2010.

International Search Report and Written Opinion for PCT/GB2008/004216 dated Jul. 2, 2009.

International Search Report and Written Opinion for PCT/GB2012/000099 dated May 2, 2012.

EP Examination Report for corresponding application 12705381.7, dated May 22, 2014.

International Search Report and Written Opinion for PCT/US2012/069893 dated Apr. 8, 2013.

International Search Report and Written Opinion for PCT/US2013/070070 dated Jan. 29, 2014.

International Search Report and Written Opinion for PCT/US2014/016320 dated Apr. 15, 2014.

International Search Report and Written Opinion for PCT/US2014/056566 dated Dec. 5, 2014.

International Search Report and Written Opinion for PCT/US2014/056508 dated Dec. 9, 2014.

International Search Report and Written Opinion for PCT/US2014/056524 dated Dec. 11, 2014.

International Search Report and Written Opinion for PCT/US2014/056594 dated Dec. 2, 2014.

International Search Report and Written opinion for PCT Application PCT/US2009/036222, mailed Dec. 15, 2009.

International Search Report and Written Opinion date mailed Oct. 19, 2010; PCT International Application No. PCT/US2009/036217.

NPD 1000 Negative Pressure Would Therapy System, Kalypto Medical, pp. 1-4, dated Sep. 2008.

International Search Report and Written Opinion for PCT/US2014/061251 date mailed May 8, 2015.

International Search Report and Written Opinion for PCT/IB2013/060862 date mailed Jun. 26, 2014.

International Search Report and Written Opinion for PCT/US2015/015493 mailed May 4, 2015.

Extended European Search Report for corresponding Application No. 15194949.2, mailed Mar. 11, 2016.

European Search Report for corresponding EPSN 15157408.4 published on Sep. 30, 2015.

International Search Report and Written Opinion for PCT/US2015/034289 mailed Aug. 21, 2015.

International Search Report and Written Opinion for PCT/US2015/065135 mailed Apr. 4, 2016.

International Search Report and Written Opinion for PCT/GB2012/050822 mailed Aug. 8, 2012.

International Search Report and Written Opinion for PCT/US2015/029037 mailed Sep. 4, 2015.

International Search Report and Written Opinion for PCT International Application No. PCT/US2011/028344, mailed Jun. 1, 2011.

European Search Report for EP 11714148.1, dated May 2, 2014.

European Search Report for corresponding Application No. 15192606.0 mailed Feb. 24, 2016.

International Search Report and Written Opinion for corresponding PCT/US2014/048081 mailed Nov. 14, 2014.

International Search Report and Written Opinion for corresponding PCT/US2014/010704 mailed Mar. 25, 2014.

European Examination Report dated Jun. 29, 2016, corresponding to EP Application No. 16173614.5.

International Search Report and Written Opinion for corresponding PCT application PCT/US2016/051768 issued Dec. 15, 2016.

European Search Report for corresponding EP Application 171572787 issued on Jun. 6, 2017.

International Search Report and Written Opinion for corresponding application PCT/US2016/031397, mailed Aug. 8, 2016.

European Search Report for corresponding application 17167872.5, mailed Aug. 14, 2017.

M. Waring et al., "Cell attachment to adhesive dressing: qualitative and quantitative analysis", Wounds, UK, (2008), vol. 4, No. 3, pp. 35-47.

R. White, "Evidence for atraumatic soft silicone wound dressing use". Wound, UK (2005), vol. 3, pp. 104-108, Mepilex Border docs, (2001).

European Search Report for corresponding application 17183683.6, mailed Sep. 18, 2017.

European Search Report for corresponding application 17164033.7, mailed Oct. 13, 2017.

Extended European Search Report for corresponding application 17191970.7, mailed Oct. 26, 2017.

Japanese office action for related application 2015-547246, mailed Sep. 5, 2017.

Office Action for related U.S. Appl. No. 13/982,650, mailed Dec. 14, 2017.

Australian Office Action for related application 2013344686, mailed Nov. 28, 2017.

(56) References Cited

OTHER PUBLICATIONS

Office Action for related U.S. Appl. No. 14/517,521, mailed Dec. 12, 2017.
Office Action for related U.S. Appl. No. 14/490,898, mailed Jan. 4, 2018.
International Search Report and Written Opinion for related application PCT/US2017/058209, mailed Jan. 10, 2018.
Office Action for related U.S. Appl. No. 14/965,675, mailed Jan. 31, 2018.
International Search Report and Written Opinion for related application PCT/US2016/047351, mailed Nov. 2, 2016.
Extended European Search Report for related application 17177013.4, mailed Mar. 19, 2018.
Extended European Search Report for related application 16793298.7, mailed Mar. 27, 2018.
Office Action for related U.S. Appl. No. 14/965,675, dated Aug. 9, 2018.
Office Action for related U.S. Appl. No. 15/307,472, dated Oct. 18, 2018.
Office Action for related U.S. Appl. No. 16/513,481, dated Mar. 30, 2022.
Office Action for related U.S. Appl. No. 16/528,441, dated May 9, 2022.
Extended European Search Report for related application 21209807.3, dated Jun. 1, 2022.
Office Action for related U.S. Appl. No. 16/733,023, dated Feb. 9, 2023.
Office Action for related U.S. Appl. No. 17/122,855, dated Feb. 7, 2023.
Office Action for related U.S. Appl. No. 16/513,481, dated Feb. 22, 2023.
Office Action for related U.S. Appl. No. 17/151,489, dated Feb. 23, 2023.
Office Action for related U.S. Appl. No. 17/374,467, dated Apr. 5, 2023.
Office Action for related U.S. Appl. No. 16/746,425, dated Aug. 17, 2023.
Office Action for related U.S. Appl. No. 16/733,023, dated Sep. 7, 2023.
Office Action for related U.S. Appl. No. 17/480,930, dated Oct. 3, 2023.
Office Action for related U.S. Appl. No. 17/226,976, dated Dec. 21, 2023.
European Examination Report for related application 21158749.8, dated Feb. 8, 2024.
Office Action for related U.S. Appl. No. 18/375,313, dated Jun. 5, 2024.
Chinese Office Action for related application 2020108367584, dated Aug. 2, 2024.
Office Action for related U.S. Appl. No. 18/220,540, dated Oct. 31, 2024.

\* cited by examiner

HYBRID SILICONE AND ACRYLIC ADHESIVE COVER FOR USE WITH WOUND TREATMENT

RELATED APPLICATIONS

This application is a Divisional of U.S. patent application Ser. No. 15/265,718, entitled "Hybrid Silicone and Acrylic Adhesive Cover for use with Wound Treatment," filed Sep. 14, 2016, which claims the benefit under 35 USC 119(e), of the filing of U.S. Provisional Patent Application No. 62/220,064, entitled "Hybrid Silicone and Acrylic Adhesive Cover for use with Wound Treatment," filed Sep. 17, 2015, which are incorporated herein by reference for all purposes.

TECHNICAL FIELD

The invention set forth in the appended claims relates generally to tissue treatment systems and more particularly, but without limitation, to a cover for use with treatment of a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of therapy can be a limiting factor in its application, and the development and operation of therapy systems, components, and processes continues to present significant benefits to healthcare providers and patients.

SUMMARY

New and useful systems, apparatuses, and methods for providing a sealed environment for negative-pressure therapy are set forth in the appended claims. Illustrative embodiments are also provided to enable a person skilled in the art to make and use the claimed subject matter.

For example, in some embodiments, a method of manufacturing a sealing member is described. A first film layer and a second film layer each having a first side and a second side can be provided. A first adhesive can be coupled to the second side of the first film layer to form a first adhesive layer. A first side of the first adhesive layer can be coupled to the second side of the first film layer. A second adhesive can be coupled to the second side of the second film layer to form a second adhesive layer. A first side of the second adhesive layer can be coupled to the second side of the second film layer. One or more perforations can be formed through the second film layer and the second adhesive layer. The first side of the second film layer can be coupled to a second side of the first adhesive layer.

More generally, a cover for a dressing of a negative-pressure therapy system is described. A bonding adhesive can be coupled to a first side of a first elastomeric film to form a bonding adhesive layer having a first side adjacent to the first side of the first elastomeric film. A sealing adhesive can be coupled to a first side of a second elastomeric film to form a sealing adhesive layer having a first side adjacent to the first side of the second elastomeric film. One or more apertures may be formed through the second elastomeric film and the sealing adhesive layer; and a second side of the sealing adhesive layer can be coupled to a second side of the bonding adhesive layer.

Alternatively, other example embodiments may describe a sealing member having a first elastomeric film having a first side and a second side, a bonding adhesive layer coupled to the first elastomeric film, a second elastomeric film having a first side and a second side and coupled to the bonding adhesive layer, and a sealing adhesive layer coupled to the second elastomeric film. The sealing adhesive layer and the second elastomeric film may have a plurality of perforations extending through the second elastomeric film and the sealing adhesive layer. The sealing member may be formed by coupling a bonding adhesive to the second side of the first elastomeric film to form the bonding adhesive layer having a first side coupled to the second side of the first elastomeric film and a second side. A sealing adhesive may be coupled to the second side of the second elastomeric film to form the sealing adhesive layer having a first side coupled to the second side of the second elastomeric film and a second side. One or more perforations may be formed through the second elastomeric film and the sealing adhesive layer. The second side of the bonding adhesive layer may be positioned proximate to the first side of the second elastomeric film, and the first side of the second elastomeric film may be coupled to the second side of the bonding adhesive layer.

A tissue cover is also described herein. The tissue cover can include a first film layer having a first side and a second side, a first adhesive layer coupled to the first film layer, and a second adhesive layer coupled to the first adhesive, the second adhesive layer having a plurality of perforations extending through the second adhesive layer. The tissue cover can be formed by coupling a first adhesive to the second side of the first film layer to form the first adhesive layer having a first side adjacent to the second side of the first film layer. A second adhesive can be coupled to a second film layer to form the second adhesive layer having a first side adjacent to the second film layer. One or more perforations can be formed through the second film layer and the second adhesive layer; and a second side of the second adhesive layer can be coupled to a second side of the first adhesive layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

Figure 1:
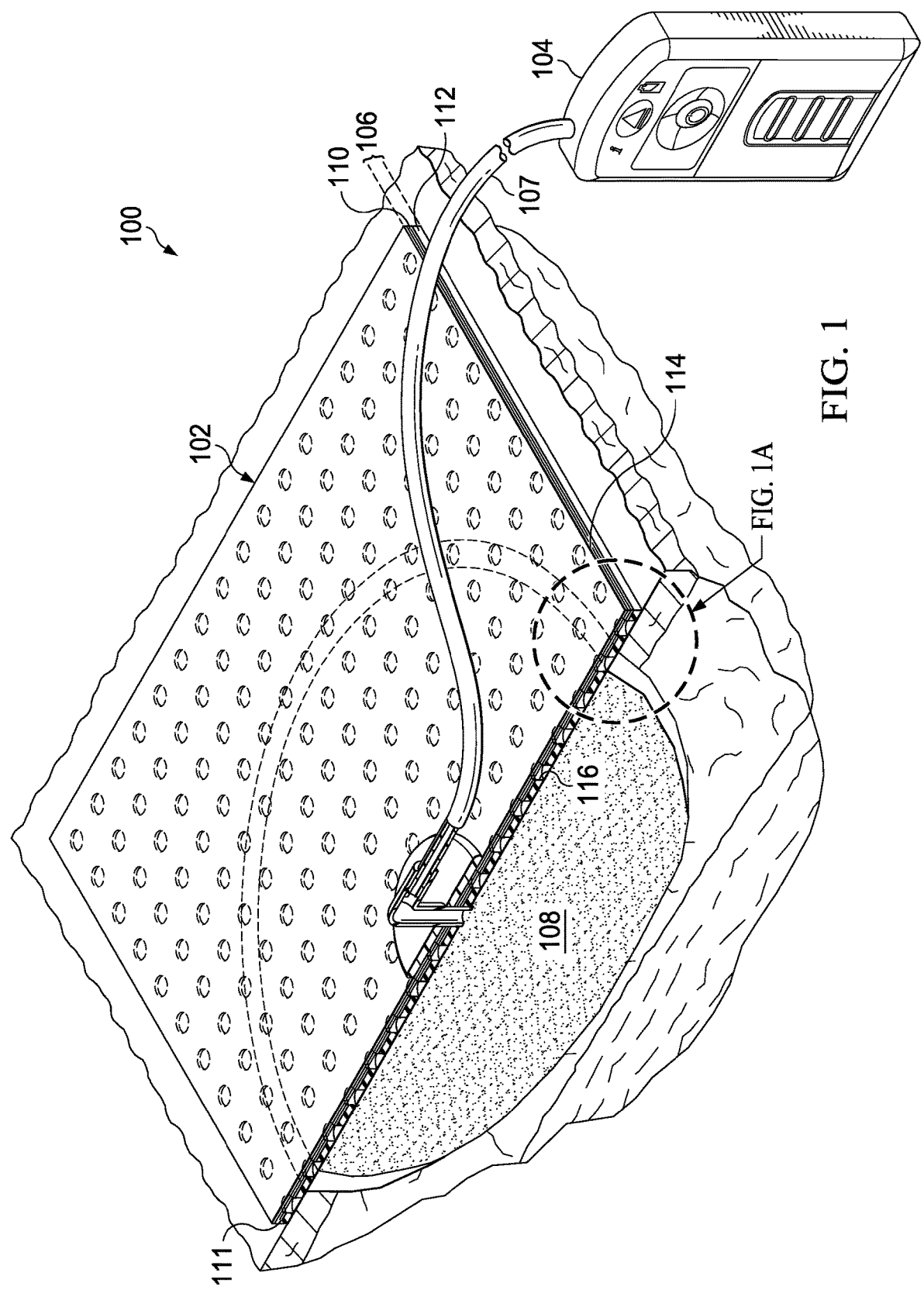
FIG. 1 is a sectional view with a portion shown in elevation of an example embodiment of a therapy system that can provide a sealed therapeutic environment in accordance with this specification.

FIG. 1 is a sectional view with a portion shown in elevation of an example embodiment of a therapy system 100 for negative-pressure therapy in accordance with this specification. The therapy system 100 may include a negative-pressure supply, such as a negative-pressure source 104, and may include or be configured to be coupled to a distribution component, such as a dressing 102. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, the dressing 102 may be fluidly coupled to the negative-pressure source 104, as illustrated in FIG. 1. A dressing may include a tissue cover, a tissue interface, or both in some embodiments. The dressing 102, for example, may include a cover 106 and a tissue interface 108. A regulator or a controller may also be coupled to the negative-pressure source 104.

In some embodiments, a dressing interface may facilitate coupling the negative-pressure source 104 to the dressing 102. For example, a dressing interface may be a T.R.A.C.® Pad or Sensa T.R.A.C.® Pad available from Kinetic Concepts, Inc. of San Antonio, Texas.

The therapy system 100 may optionally include a fluid container coupled to or integral with the dressing 102 and to the negative-pressure source 104. A fluid container may include a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

Additionally, the therapy system 100 may include sensors to measure operating parameters and provide feedback signals to a controller of the negative-pressure source 104. The feedback signals can be indicative of the operating parameters, such as pressure at the tissue site, humidity at the tissue site, or temperature at the tissue site, for example. The therapy system 100 may include a pressure sensor, a humidity sensor, a temperature sensor, or the like. In some embodiments, the sensors may be electrical sensors that can communicate with the therapy system 100 through electric signals. In other embodiments, the sensors may be pneumatically or hydraulically operated. A pressure sensor may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube 107. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to a container.

In general, components of the therapy system 100 may be coupled to each other directly or indirectly. For example, the negative-pressure source 104 may be directly coupled to the dressing 102 or indirectly coupled to the dressing 102 through a container.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mmHg (−667 Pa) and −500 mmHg (−66.7 kPa). Common therapeutic ranges are between −75 mmHg (−9.9 kPa) and −300 mmHg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with a controller and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a negative-pressure supply and distribute negative pressure through multiple apertures across a tissue site, which may have the effect of collecting fluid from across a tissue site and drawing the fluid toward a negative-pressure supply. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of about 400 to about 600 microns. The tensile strength of the tissue interface 108 may also vary according to the needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or VeraFlo® foam, both available from Kinetic Concepts, Inc. of San Antonio, Texas.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within a sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 1A:
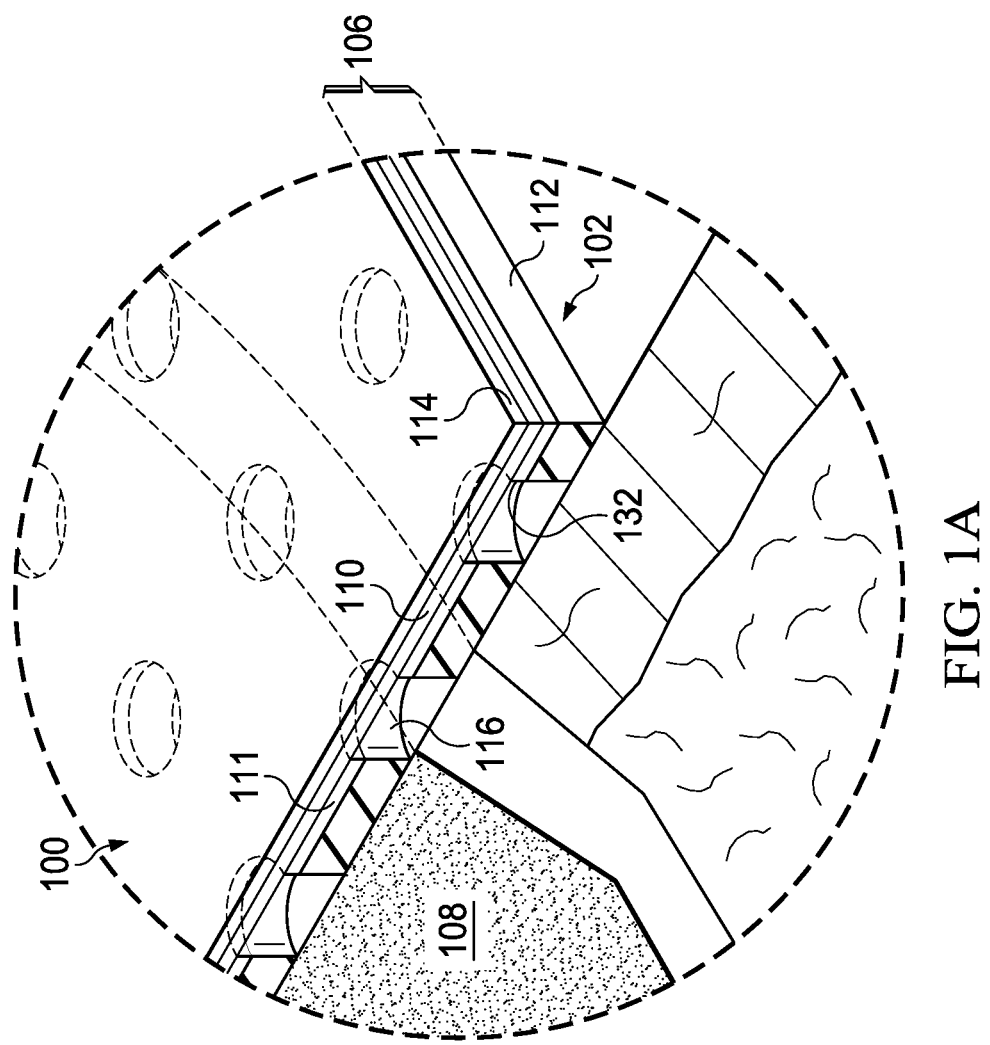
FIG. 1A is a detail view of a portion of a cover of the therapy system of FIG. 1 illustrating additional details that may be associated with some embodiments.

In some embodiments, the cover 106 may be a sealing member configured to provide a bacterial barrier and protection from physical trauma. The cover 106 may also be constructed from a material that can reduce evaporative losses and provide a fluid seal between two components or two environments, such as between a therapeutic environment and a local external environment. FIG. 1A is a detail view of a portion of the therapy system 100 of FIG. 1, illustrating additional details that may be associated with the cover 106. The cover 106 may be, for example, a film layer 114 or membrane that can provide a seal adequate to maintain a negative pressure at a tissue site for a given negative-pressure source. The cover 106 may have a high moisture-vapor transmission rate (MVTR) in some applications. For example, the MVTR may be at least about 300 g/m$^2$ per twenty-four hours. In some embodiments, the cover 106 may be a polymer cover, such as a polyurethane film, that is permeable to water vapor but impermeable to liquid. Such covers typically have a thickness in the range of about 25 to about 50 microns. For permeable materials, the permeability generally should be low enough that a desired negative pressure may be maintained.

The cover 106 may include an attachment device to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between about 25 and about 65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the attachment device may comprise a first adhesive layer 110 and a second adhesive layer 112. The first adhesive layer 110 may be a continuous adhesive layer and may be secured to the film layer 114. The second adhesive layer 112 may be secured to the first adhesive layer 110 and have a plurality of apertures 116 extending through the second adhesive layer 112. In some embodiments, a support layer 111 may be disposed between the second adhesive layer 112 and the first adhesive layer 110. In some embodiments, the support layer 111 may have a plurality of apertures 132.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site that is substantially isolated from the external environment. The negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in a container.

In some embodiments, a battery or other portable power supply may supply power to the negative-pressure source 104. Use of battery power can significantly decrease the total power available to a negative-pressure supply. As a result, power drains that would be considered negligible in a device powered through an electrical outlet connection may significantly reduce the ability of the negative-pressure supply to provide therapy. A power drain refers to operation of the negative-pressure supply that requires use of electrical power, for example, operation of a pump to generate negative pressure. Power drains may be caused by small dressing leaks, for example. A small dressing leak can drain power from a battery of a negative-pressure supply by repeatedly triggering operation of the negative-pressure supply to maintain the necessary negative pressure at the tissue site. These power drains shorten the useful life of the negative-pressure supply before disposal of the negative-pressure supply, recharge of the battery, or battery replacement is required. Leak detection techniques may help to identify some leaks that may then be sealed by the user; however, small leaks will challenge the most sensitive leak detection systems and may often go undetected.

Small leaks may occur between the cover and the epidermis surrounding a tissue site if the cover fails to completely seal to the epidermis. Covers can be a balance between the strength of the attachment device required to enable the cover to seal against leaks and the pain which may result if the cover is removed. Generally, adhesives used to form the attachment device can be loosely classified as "bonding" adhesives or "sealing" adhesives.

A bonding adhesive is generally stronger than a sealing adhesive. A bonding adhesive may also provide a suitable seal, but the strength of a bonding adhesive can cause significantly more discomfort upon removal. In addition, removing a cover with a bonding adhesive may cause significant damage to patients having delicate or damaged skin.

A sealing adhesive can generally be characterized by lower strength and lower viscosity than a bonding adhesive. A cover that has a sealing adhesive can fill gaps between the cover and the epidermis to limit leaks and can be easy to remove with low discomfort to the patient. Various sealing, gap-filling adhesives, such as silicone, hydrocolloids, and hydrogels, have been tried but each has drawbacks. For example, hydrogel adhesives are usually low tack and prone to swelling, creep, and mobility when used with fluid systems. In another example, silicone adhesives can fill gaps and seal, but are not breathable and may lose the necessary mechanical bonding strength as the silicone adhesives interact with moisture during use. To counter these problems, silicone adhesives often require additional materials to secure the silicone adhesive to the patient. For example, a low-leak cover may be formed from two adhesive layers: a thick sealing adhesive, perhaps in the shape of a gasket or ring, and a thinner bonding adhesive layer used to keep the sealing adhesive in place. The thinner bonding adhesive may be applied as cover strips, or combined with the thicker sealing adhesive as an outer border. Low-leak covers constructed in this way can be more complex than a cover using a single adhesive, increasing the complexity of manipulation and operation.

A hybrid cover having a thick sealing layer that is perforated and laminated over an adhesive-coated film can overcome some of these challenges. For example, a hybrid cover may include a film layer having a bonding adhesive applied directly to the film layer, and a sealing adhesive applied directly to the bonding adhesive. The bonding adhesive and the sealing adhesive can be laminated to the film layer by applying the bonding adhesive and the sealing adhesive to the film layer in a liquid form and the curing the bonding adhesive and the sealing adhesive in place on the film layer. Curing may involve toughening or hardening of polymer material by cross-linking of polymer chains within the polymer material. Curing can include the addition of heat, chemical additives and ultraviolet radiation to cause cross-linking within the polymer material. After lamination, the sealing adhesive can be perforated to expose the bonding adhesive. If the cover is applied to a patient, the bonding adhesive can be pushed through the perforations of the sealing adhesive to secure the sealing adhesive to the patient. This laminated configuration may provide the benefits of the sealing adhesive and the bonding adhesive over the entire cover area. For example, the laminated configuration may be conformable and of sufficient strength to seal small leaks, and can be mechanically affixed to an epidermis without secondary processes. The laminated configuration can also be removable with minimal trauma to the patient.

However, construction of a laminated attachment device may require a complicated manufacturing process. For example, to form the sealing layer, a thick sealing adhesive may be applied to a scrim layer. A scrim layer may be a sheet of strong, coarse fabric or webbing. The sealing adhesive may be cast onto the scrim layer and cured around the scrim layer. Casting involves pouring a liquid material, for example an adhesive, into a mold having a hollowed cavity of the desired shape. The liquid material is allowed to solidify or cure into a solid or semi-solid body. The scrim layer may provide support for the sealing adhesive and can aid in the manipulation of the sealing adhesive during the manufacturing process. After casting the sealing adhesive onto the scrim layer, the sealing adhesive and scrim layer may be coupled to an adhesive coated film layer to form a cover.

Moreover, fabric in the scrim layer can inhibit the light transmittance of the cover by increasing the absorbance of the cover. For example, the scrim layer may be a barrier in the cover that can absorb light. The scrim layer may also reflect light transmitting through the cover, or scatter light reflecting through the cover, causing the light to be attenuated by the cover. As the light is absorbed, reflected or scattered, the light cannot reflect off of a wound covered by the cover. As a consequence, the scrim layer may cause the cover to appear opaque and prevent a clinician from seeing through the cover to view the dressing or tissue site.

The scrim layer may also add additional thickness to the sealing layer. If the scrim layer is exposed, the exposed portions may prevent the sealing layer from forming an effective seal between the cover and the epidermis. As a result, additional sealing adhesive may be needed to ensure that the scrim layer is not exposed. The coarse fabric or webbing of a scrim layer may also have large openings between threads of the fabric or webbing. If the sealing adhesive is cast onto the scrim layer, the sealing adhesive may need to fill the openings in the fabric. As a result, if a scrim layer is used, even more sealing adhesive may be needed to completely cover the scrim layer and provide a surface for adhesion of the sealing adhesive to a patient. The scrim layer, along with any additional sealing adhesive needed, may add stiffness to the cover, reducing the conformability of the cover and inhibiting the ability of the sealing adhesive to migrate and seal to tissue.

As disclosed herein, these challenges and others can be overcome with a cover having a hybrid configuration with a sealing adhesive layer and a bonding adhesive layer that can be constructed without the use of a scrim layer. Light transmittance can also be improved to provide accurate cover positioning and visualization of the tissue interface and periwound during treatment. In some embodiments, flexibility and conformability can be increased, and adhesives used more efficiently when manufacturing the cover. Increased efficiency of adhesive use may enable a thinner coating of adhesive, which can decrease the cost.

Figure 2:
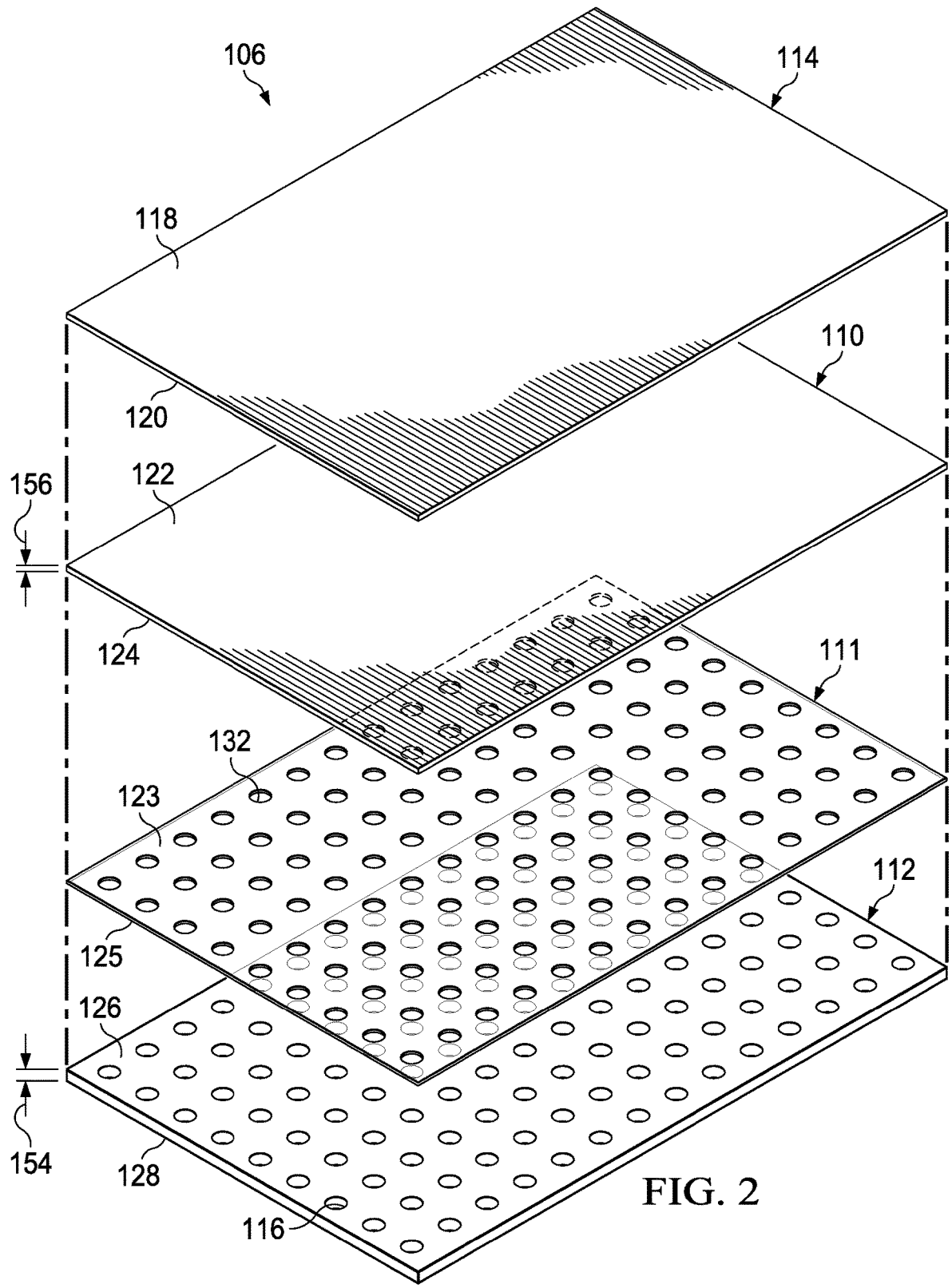
FIG. 2 is a perspective exploded view of the cover of the therapy system of FIG. 1.

FIG. 2 is a perspective exploded view of an example embodiment of the cover 106. The cover 106 may include the film layer 114, the first adhesive layer 110 adjacent to the film layer 114, the support layer 111 adjacent to the first adhesive layer 110, and the second adhesive layer 112 adjacent to the support layer 111. The film layer 114 may be formed from a range of medically approved films ranging in thickness from about 15 microns ($\mu$m) to about 50 microns ($\mu$m). The film layer 114 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the film layer 114 may be formed from a breathable cast matt polyurethane film sold by Expopack Advanced Coatings of Wrexham, United Kingdom, under the name INSPIRE™ 2301 or INSPIRE™ 2327.

The film layer 114 may have a high moisture-vapor-transfer-rate (MVTR). A high MVTR may allow vapor to egress the sealed therapeutic environment through the film layer 114 and inhibit liquids from exiting the sealed therapeutic environment through the film layer 114. In some embodiments, the MVTR of the film layer 114 may be greater than or equal to about 300 grams per meter squared per twenty-four hours ($g/m^2/24$ hours). In other embodiments, the MVTR of the film layer 114 may be greater than or equal to about 1000 $g/m^2/24$ hours. The illustrative INSPIRE™ 2301 film may have an MVTR (tested using the inverted cup technique) of about 14400 $g/m^2/24$ hours and may be about 30 microns thick. In other embodiments, a film having a low MVTR or that allows no vapor transfer might be used. The film layer 114 can also function as a barrier to microorganisms.

The film layer 114 may have a first side 118 and a second side 120. The first adhesive layer 110 may also have a first side 122 and a second side 124. The first side 122 of the first adhesive layer 110 may face the second side 120 of the film layer 114. In some embodiments, the first adhesive layer 110 may be a medically-acceptable, pressure-sensitive adhesive, glue, bonding agent, or cement. For example, the first adhesive layer 110 may be formed from or include a bonding adhesive. The bonding adhesive may be a high bond strength acrylic adhesive, patternrubber adhesive, high-tack silicone adhesive, or polyurethane, for example. In some embodiments, the bond strength of the bonding adhesive may have a peel adhesion or resistance to being peeled from a stainless steel material between about 6 N/25 mm to about 10 N/25 mm on stainless steel substrate at 23° C. at 50% relative humidity based on the American Society for Testing and Materials ("ASTM") standard ASTM D3330. In some embodiments, the bonding adhesive of the first adhesive layer 110 comprises an acrylic adhesive with a coating weight of about 10 grams/m² (gsm) to about 70 grams/m² (gsm). The first adhesive layer 110 may have a thickness 156, and in some embodiments, the thickness 156 of the first adhesive layer 110 may be about 30 microns to about 60 microns.

The support layer 111 may have a first side 123 and a second side 125. In some embodiments, the first side 123 of the support layer 111 may face the second side 124 of the first adhesive layer 110. The support layer 111 may be an elastomeric film and may have a high moisture-vapor-transfer-rate (MVTR) similar to the film layer 114. The support layer 111 may be formed from a range of medically-approved films ranging in thickness from about 15 microns (μm) to about 50 microns (μm). The support layer 111 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In some embodiments, the support layer 111 may be formed from a breathable cast matt polyurethane film sold by Expopack Advanced Coatings of Wrexham, United Kingdom under the name INSPIRE 2301 or INSPIRE 2327.

In some embodiments, the MVTR of the support layer 111 may be greater than or equal to about 300 $g/m^2/24$ hours. In other embodiments, the MVTR of the support layer 111 may be greater than or equal to about 1000 $g/m^2/24$ hours. The illustrative INSPIRE™ 2301 film may have an MVTR (inverted cup technique) of about 14400 $g/m^2/24$ hours and may be about 30 microns thick. In other embodiments, a support layer having a low MVTR or that allows no vapor transfer might be used. The support layer 111 can also function as a barrier to liquids and microorganisms.

In some embodiments, the support layer 111 may have a plurality of apertures 132. Each aperture 132 of the plurality of apertures 132 may extend through the support layer 111 from the first side 123 to the second side 125. The plurality of apertures 132 may be numerous shapes, including without limitation, circles, squares, stars, ovals, polygons, slits complex curves, rectilinear shapes, or triangles. Each aperture 132 of the plurality of apertures 132 may have an effective diameter. An effective diameter of a non-circular area is the diameter of a circular area having the same area as the non-circular area. The average effective diameter is typically in the range of about 4 mm to about 50 mm. The plurality of apertures 132 may have a uniform pattern or may be randomly distributed on the support layer 111. In some embodiments, the apertures 132 may be distributed so that centers of adjacent apertures 132 may be separated by between about 5 mm and about 100 mm. In other embodiments, the apertures 132 may be distributed so that the centers of adjacent apertures 132 may be separated by about 10 mm.

Regardless of the shape of the plurality of apertures 132, the plurality of apertures 132 in the support layer 111 may leave void spaces in the support layer 111. The percentage of void space of the plurality of apertures 132 may be equal to the percentage of the volume or surface area of the void spaces created by the plurality of apertures 132 to the total volume or surface area of the support layer 111. In some embodiments, the percentage of void space may be between about 40% and about 75%. In other embodiments, the percentage of void space may be about 55%. The organization of the plurality of apertures 132 can also impact the percentage of void space. The plurality of apertures 132 may be formed by punching, cutting, melting, or drilling the support layer 111.

The second adhesive layer 112 may have a first side 126 and a second side 128. The first side 126 of the second adhesive layer 112 may face the second side 125 of the support layer 111 and have a thickness 154. The second adhesive layer 112 may be formed from or include a sealing adhesive. The sealing adhesive may be an adhesive having a low to medium tackiness, for example, a silicone polymer, polyurethane, or an additional acrylic adhesive. Generally, tackiness may be understood as a bond strength of an adhesive after a very short contact time between the adhesive and a substrate, such as less than 60 seconds. In some embodiments, the bond strength of the sealing adhesive may have a peel adhesion or resistance to being peeled from a stainless steel material between about 0.5 N/25 mm to about 1.5 N/25 mm on stainless steel substrate at 23° C. at 50% relative humidity based on ASTM D3330. The sealing adhesive may achieve its bond strength above after a contact time with the substrate of less than 60 seconds. In some embodiments, the sealing adhesive may have a coating weight between about 150 gsm and about 250 gsm, be about 100 microns to about 400 microns thick, and have a tackiness that may be about 30% to about 50% of the tackiness of the bonding adhesive that may be used in the first adhesive layer 110. In some embodiments a catalyst may be added to the sealing adhesive to provide additional therapeutic properties; for example, a platinum catalyst or a sulfur catalyst may be added to the sealing adhesive to aid in treatment.

In some embodiments, the second adhesive layer 112 may have a plurality of apertures 116 that extend through the second adhesive layer 112 from the first side 126 to the second side 128. The plurality of apertures 116 may be, for example, circles, squares, stars, ovals, polygons, slits, complex curves, rectilinear shapes, triangles, or other shapes. Each aperture 116 of the plurality of apertures 116 may have an effective diameter typically in the range of about 4 mm to about 50 mm. The plurality of apertures 116 may have a uniform pattern or may be randomly distributed on the second adhesive layer 112. In some embodiments, the apertures 116 may be distributed so that centers of adjacent apertures 116 may be separated by between about 5 mm and about 100 mm. In other embodiments, the apertures 116 may be distributed so that the centers of adjacent apertures 116 may be separated by about 10 mm.

Regardless of the shape of the plurality of apertures 116, the plurality of apertures 116 in the second adhesive layer 112 may leave void spaces in the second adhesive layer 112. The percentage of void space of the plurality of apertures 116 may be equal to the percentage of the volume or surface area of the void spaces created by the plurality of apertures 116 to the total volume or surface area of the second adhesive layer 112. In some embodiments, the percentage of void space may be between about 40% and about 75%. In other embodiments, the percentage of void space may be about 55%. The organization of the plurality of apertures 116 can also impact the percentage of void space. The plurality of apertures 116 may be formed by punching, cutting, melting, or drilling, for example.

Figure 3:
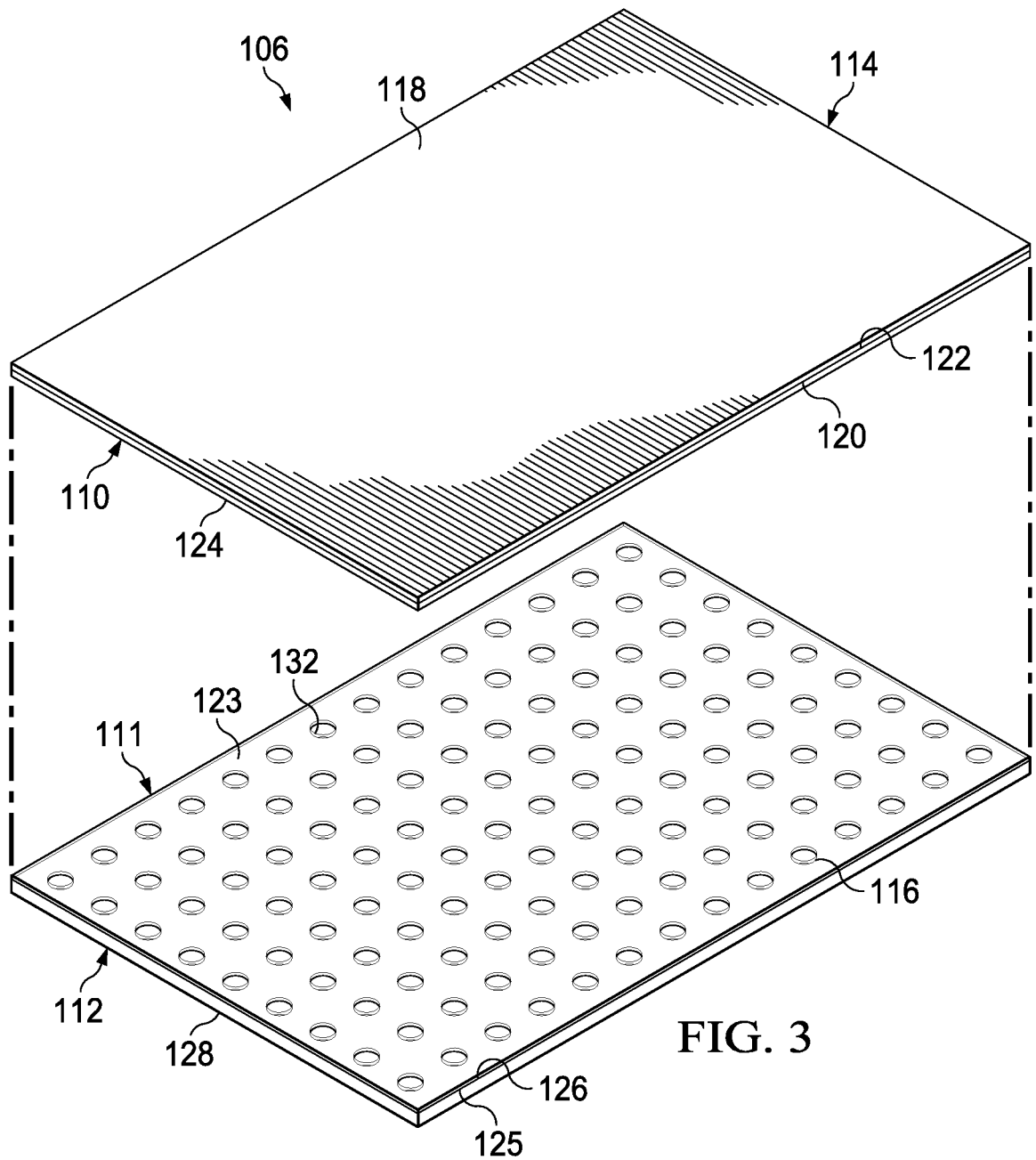
FIG. 3 is a perspective partially assembled view of the cover of FIG. 2 illustrating additional details that may be associated with some embodiments.

FIG. 3 is a perspective view of the cover 106 partially assembled, illustrating additional details that may be associated with some embodiments. As shown in FIG. 3, the film layer 114 may be coupled to the first adhesive layer 110. For example, the second side 120 of the film layer 114 may be in contact with and coupled to the first side 122 of the first adhesive layer 110. The film layer 114 and the first adhesive layer 110 may be coextensive. For example, the second side 120 of the film layer 114 and the first side 122 of the first adhesive layer 110 may be in contact across the entirety of their respective surface areas. The film layer 114 may be coupled to the first adhesive layer 110 by bonding, adhering, welding, or cross-linking, for example.

Similarly, the support layer 111 may be coupled to the second adhesive layer 112. For example, the second side 125 of the support layer 111 may be in contact with and coupled to the first side 126 of the second adhesive layer 112. The support layer 111 and the second adhesive layer 112 may be coextensive. For example, the first side 126 of the second adhesive layer 112 and the second side 125 of the support layer 111 may be in contact across the entirety of their respective surface areas. The support layer 111 may be coupled to the second adhesive layer 112 by bonding, adhering, welding, or cross-linking, for example. In some embodiments, the plurality of apertures 132 may be distributed in the support layer 111 so that the plurality of apertures 132 are aligned with the plurality of apertures 116 of the second adhesive layer 112 if the support layer 111 and the second adhesive layer 112 are coupled. For example, each aperture 132 of the support layer 111 may be aligned with a corresponding aperture 116 of the second adhesive layer 112.

Figure 4A:
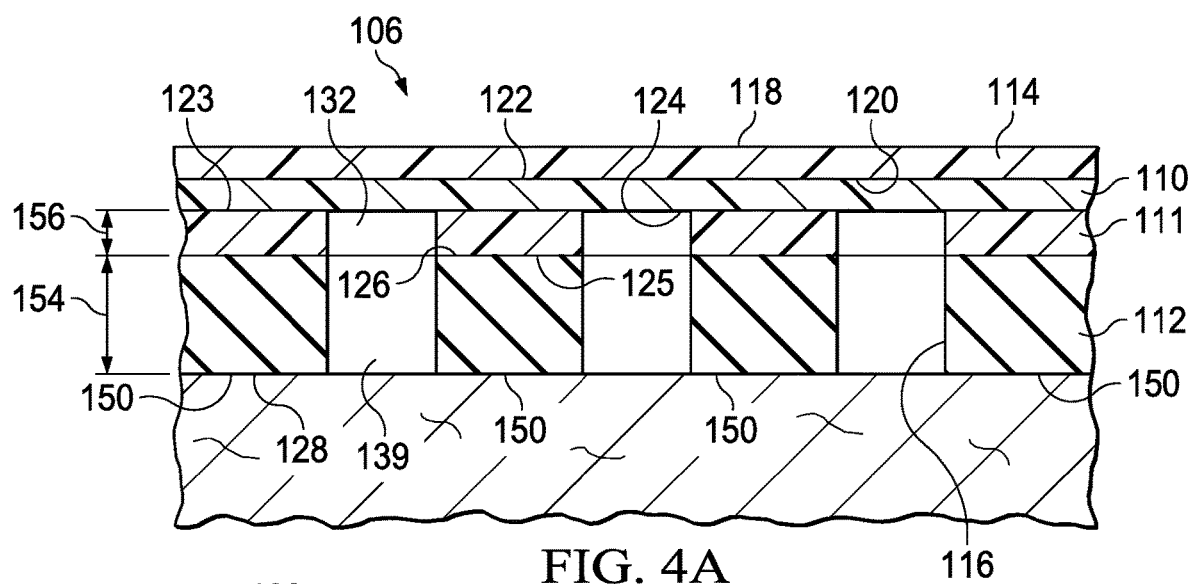
FIG. 4A is a sectional view of the cover of FIG. 2 illustrating additional details that may be associated with the cover in a first position.

FIG. 4A is a schematic view of the assembled cover 106 in a first position on the epidermis, illustrating additional details that may be associated with some embodiments. The second side 120 of the film layer 114 may be coupled to first side 122 of the first adhesive layer 110. The second side 124 of the first adhesive layer 110 may be coupled to the first side 123 of the support layer 111. And the second side 125 of the support layer 111 may be coupled to the first side 126 of the second adhesive layer 112. The cover 106 may be disposed over the epidermis to form the sealed therapeutic environment. The tackiness of the sealing adhesive of the second adhesive layer 112 may form sealing couplings 150 between the second side 128 of the second adhesive layer 112 and the epidermis to hold the cover 106 in an initial position as illustrated in FIG. 4A. The tackiness of the sealing adhesive of the second adhesive layer 112 may be such that the cover 106 may be removed and reapplied or repositioned. In some embodiments, the thickness 154 of the second adhesive layer 112 may prevent the first adhesive layer 110 from contacting the epidermis, forming a gap 139 between the first adhesive layer 110 and the epidermis.

Figure 4B:
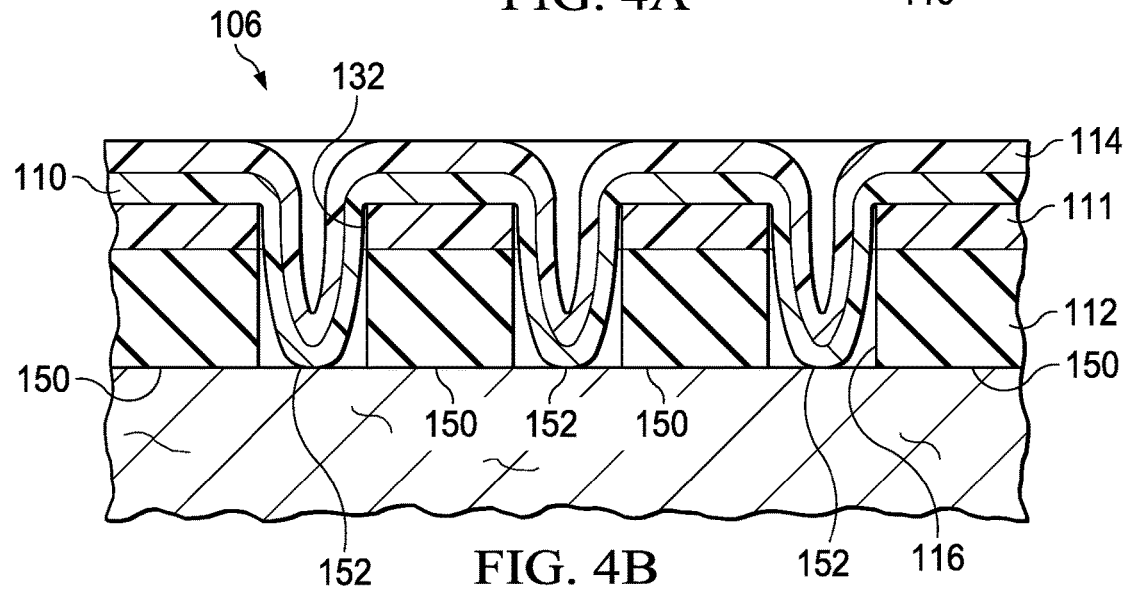
FIG. 4B is a sectional view of the cover of FIG. 2 illustrating additional details that may be associated with the cover in a second position.

FIG. 4B is a schematic view of the cover 106 in a second position, illustrating additional details that may be associated with some embodiments. If the cover 106 is placed at a tissue site, a force may be applied to the first side 118 of the film layer 114. The force may cause at least some portion of the bonding adhesive of the first adhesive layer 110 to move through the apertures 116. In response, the second side 124 of the first adhesive layer 110 may contact the epidermis and form bonding couplings 152, as illustrated in the second position of FIG. 4B. For example, the bonding couplings 152 may be located where the second side 124 of the first adhesive layer 110 adheres to the epidermis. In some embodiments, the bonding couplings 152 may have a peel force against the epidermis between about 0.5 N/25 mm and about 2 N/25 mm.

The average effective diameter of the plurality of apertures 116 for the second adhesive layer 112 may be varied as one control of the tackiness or adhesion strength of the cover 106. Generally, the strength of the bond of the bonding coupling 152 is proportional to the effective diameter of the plurality of apertures 116 of the second adhesive layer 112, the thickness 154 of the second adhesive layer 112, and the tackiness of the first adhesive layer 110. The more of the first adhesive layer 110 that extends through the apertures 116, the more bonding adhesive of the first adhesive layer 110 contacts the epidermis and the stronger the bond of the bonding coupling 152. In some embodiments, the thickness 154 of the second adhesive layer 112 may permit more of the first adhesive layer 110 to extend through the apertures 116 and increase the bond of the bonding coupling 152. As an example of the interplay, if a first bonding adhesive is used to form the first adhesive layer 110 and the thickness 154 of the second adhesive layer 112 is a first thickness, the average effective diameter of the plurality of apertures 116 may be a first effective diameter so that the bonding couplings 152 have a first bond strength. If the thickness 154 of the second adhesive layer 112 is increased to be larger than the first thickness, the average effective diameter may increase to be larger than the first effective diameter to achieve the first bond strength of the bonding coupling 152. In some embodiments, the thickness 154 may be about 200 microns, the first adhesive layer 110 may be about 30 microns with a bonding adhesive having a tackiness of about 2000 g/25 cm wide strip, and the average effective diameter of each aperture 116 of the plurality of apertures 116 may be about 6 mm.

Figure 5A:
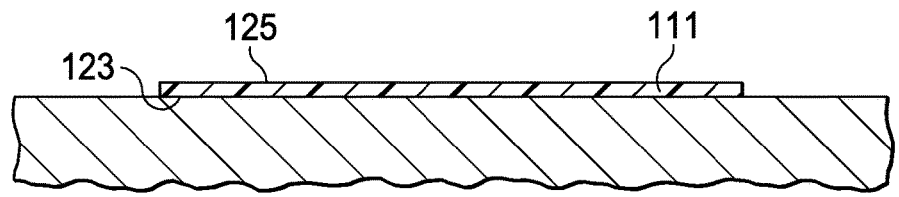
FIGS. 5A-5F are schematic views illustrating additional details that may be associated with an assembly process of the cover of FIG. 2.

The cover 106 can be manufactured in many ways including by following the operations provided below to produce the cover 106 without a scrim layer. The operations can be performed using manufacturing processes and equipment to manipulate the materials as described below. FIG. 5A is a schematic view illustrating additional details that may be associated with some embodiments of the manufacturing process of the cover 106. In some embodiments, the support layer 111 may be provided and suitably disposed so that the first side 123 is supported by a suitable surface, and the second side 125 is exposed.

Figure 5B:
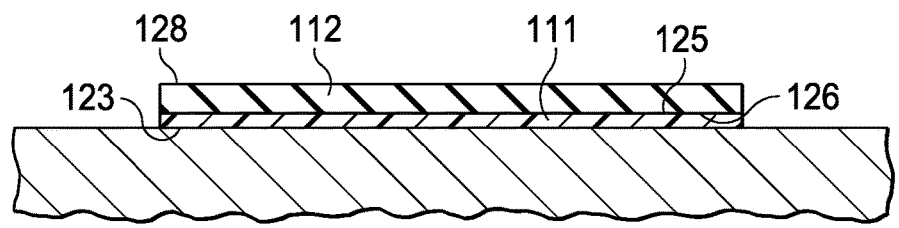

FIG. 5B is a schematic view illustrating additional details that may be associated with some embodiments of the manufacturing process of the cover 106. A sealing adhesive may be cast onto the second side 125 of the support layer 111. In some embodiments, the sealing adhesive may be cured or otherwise cross-linked to form the second adhesive layer 112 and couple the second adhesive layer 112 to the second side 125 of the support layer 111. In some embodiments, the sealing adhesive of the second adhesive layer 112 may be a two-part silicone system, such as those provided by Wacker, Dow, or NuSil. To cure, the two-part silicone system may be heated once applied to the second side 125 of the support layer 111. Heating may encourage cross-linking or curing to cause the two-part silicone system to form a gel. In other embodiments, the sealing adhesive may be a one-part silicone system, and the sealing adhesive may be cured or cross-linked by exposing the one-part silicone system to ultraviolet light or ionizing radiation.

In other embodiments, the support layer 111 may be laminated to the second adhesive layer 112. For example, the sealing adhesive of the second adhesive layer 112 may be cast and cured as described above. After the sealing adhesive has cured to form the second adhesive layer 112, the support layer 111 may be laminated to the second adhesive layer 112.

Figure 5C:
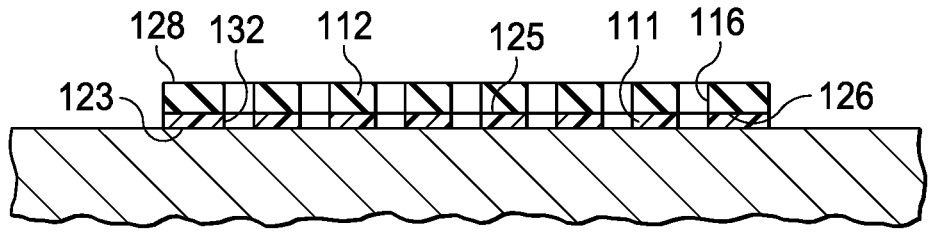

FIG. 5C is a schematic view illustrating additional details that may be associated with some embodiments of the manufacturing process of the cover 106. The plurality of apertures 116 and the plurality of apertures 132 may be formed following casting of the second adhesive layer 112 onto the support layer 111. In some embodiments, the apertures 116 and the apertures 132 may be formed using shaped pins that puncture the support layer 111 and the second adhesive layer 112 as the support layer 111 and the second adhesive layer 112 move along a manufacturing path. In other embodiments, the apertures 116 and the apertures 132 may be formed by rolling a drum having shaped pins along the support layer 111 and the second adhesive layer 112. The shaped pins may be configured to make the desired shape and size of the apertures 116 and the apertures 132. In other embodiments, the apertures 116 and the apertures 132 may be cut or torn. For example, a punch may be used to puncture the support layer 111 and the second adhesive layer 112. The apertures 116 and the apertures 132 may also be formed by melting portions of the support layer 111 and the second adhesive layer 112. For example, a heated element, such as a poker may be applied to the support layer 111 and the second adhesive layer 112, melting portions of the support layer 111 and the second adhesive layer 112. In some embodiments, the apertures 116 and the apertures 132 may be formed in the second adhesive layer 112 and the support layer 111, respectively, prior to the coupling of the support layer 111 and the second adhesive layer 112 to each other.

In some embodiments, a mold may be used to form the second adhesive layer 112. For example, the sealing adhesive may be cast into a mold having projections that extend into the sealing adhesive. After the sealing adhesive is cured, the mold and projections may be removed, leaving the apertures 116 formed in the second adhesive layer 112. The support layer 111 may then be laminated to the second adhesive layer 112. If the apertures 116 are formed with a mold, the apertures 132 may be separately formed in the support layer 111.

Figure 5D:
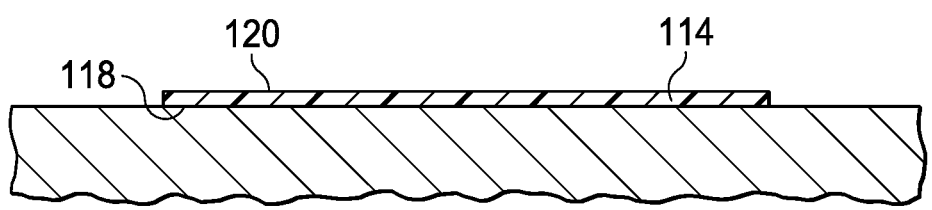

FIG. 5D is a schematic view illustrating additional details that may be associated with some embodiments of the manufacturing process of the cover 106. In the example embodiment of FIG. 5D, the film layer 114 may be provided and positioned so that the first side 118 is supported by a suitable surface and the second side 120 is exposed.

Figure 5E:
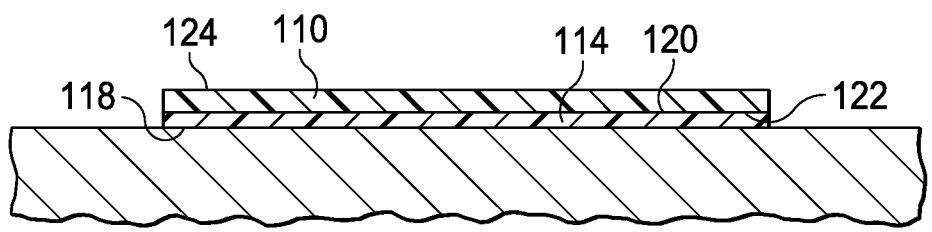

FIG. 5E is a schematic view illustrating additional details that may be associated with some embodiments of the manufacturing process of the cover 106. For example, the first adhesive layer 110 may be cast onto the second side 120 of the film layer 114 of FIG. 5D. In other embodiments, the first adhesive layer 110 may be cast and cured, and the film layer 114 may then be laminated to the first adhesive layer 110.

Figure 5F:
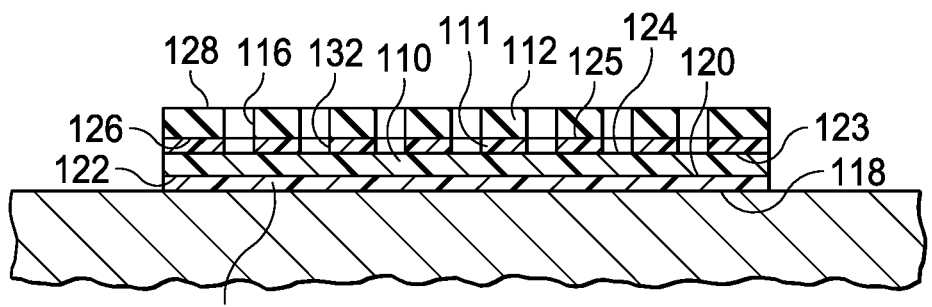

FIG. 5F is a schematic view illustrating additional details that may be associated with some embodiments of the manufacturing process of the cover 106. The support layer 111 and the second adhesive layer 112 may be positioned so that the first side 123 of the support layer 111 is proximate to the second side 124 of the first adhesive layer 110 of FIG. 5E. The first side 123 of the support layer 111 may be coupled to the second side 124 of the first adhesive layer 110 to form the cover 106 as shown in the example of FIG. 5F. In other embodiments, the second side 124 of the first adhesive layer 110 may be brought proximate to the first side 123 of the support layer 111. The second side 124 of the first adhesive layer 110 may then be coupled to the first side 123 of the support layer 111, forming the cover 106.

Figure 6:
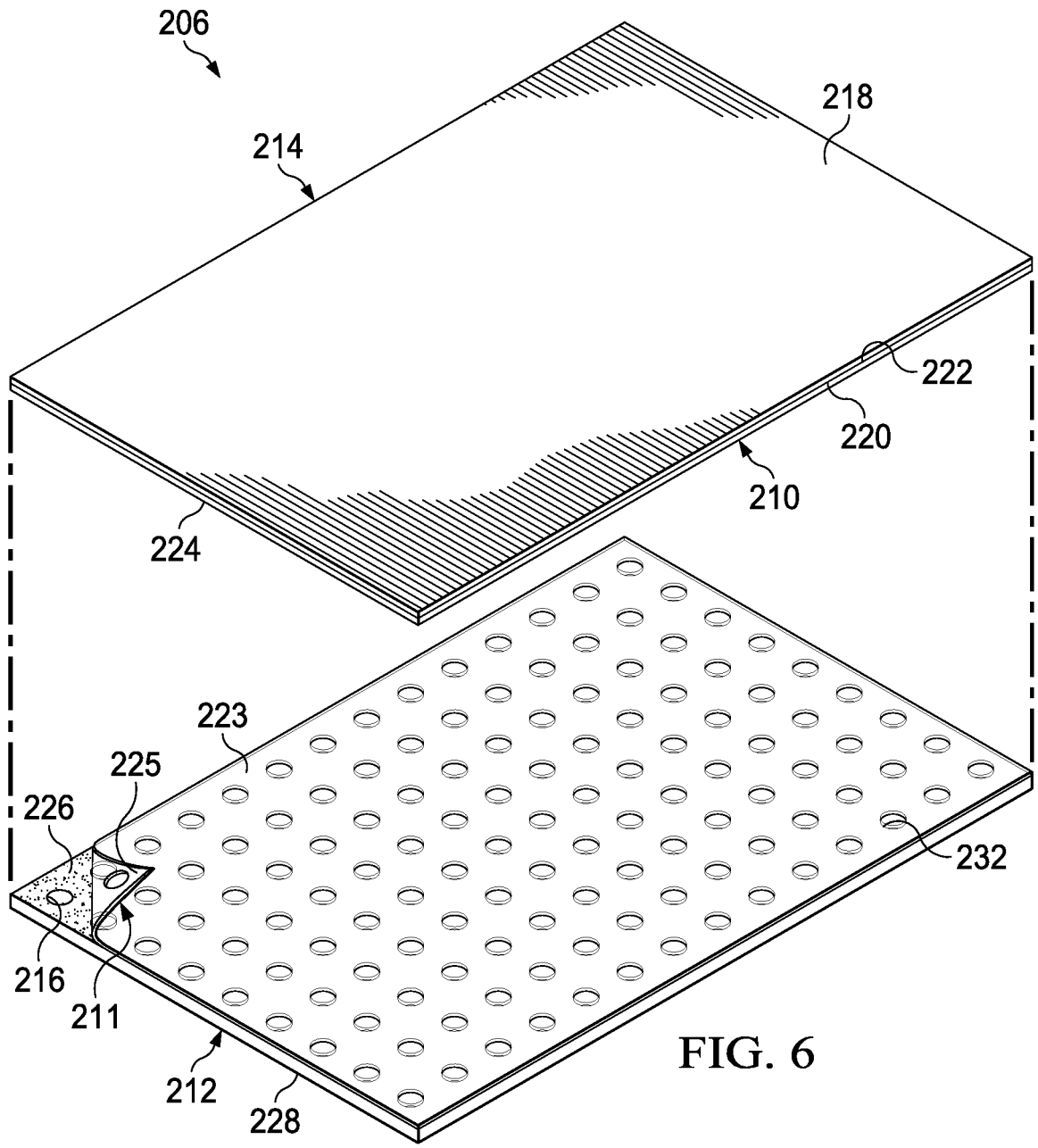
FIG. 6 is a perspective view illustrating additional details that may be associated with another cover that may be used with the therapy system of FIG. 1.

FIG. 6 is perspective view of a cover 206 partially assembled, which may be associated with some embodiments of the therapy system 100 of FIG. 1, for example. The cover 206 may be similar to the cover 106 as described above with respect to FIGS. 1-5F. Similar elements may have similar reference numbers that are indexed to 200. As shown in FIG. 6, a film layer 214 may be coupled to a first adhesive layer 210. For example, a second side 220 of the film layer 214 may be in contact with and coupled to a first side 222 of the first adhesive layer 210. The film layer 214 and the first adhesive layer 210 may be coextensive. The film layer 214 may be coupled to the first adhesive layer 210 by bonding, adhering, welding, or cross-linking, for example.

Similarly, a support layer 211 may be coupled to a second adhesive layer 212. For example, a second side 225 of the support layer 211 may be in contact with and coupled to a first side 226 of the second adhesive layer 212. The support layer 211 and the second adhesive layer 212 may be coextensive. The support layer 211 may be coupled to the second adhesive layer 212 by bonding, adhering, welding, or cross-linking, for example. In some embodiments, a plurality of apertures 232 may be distributed in the support layer 211 so that the plurality of apertures 232 are aligned with a plurality of apertures 216 of the second adhesive layer 212. The plurality of apertures 232 and the plurality of apertures 216 may be said to be coextensive so that each aperture 232 is aligned with a corresponding aperture 216.

In some embodiments, the support layer 211 may be removed prior to final assembly of the cover 206. For example, as shown in FIG. 5, the support layer 211 may be removed by peeling the support layer 211 from the second adhesive layer 212.

Figure 7:
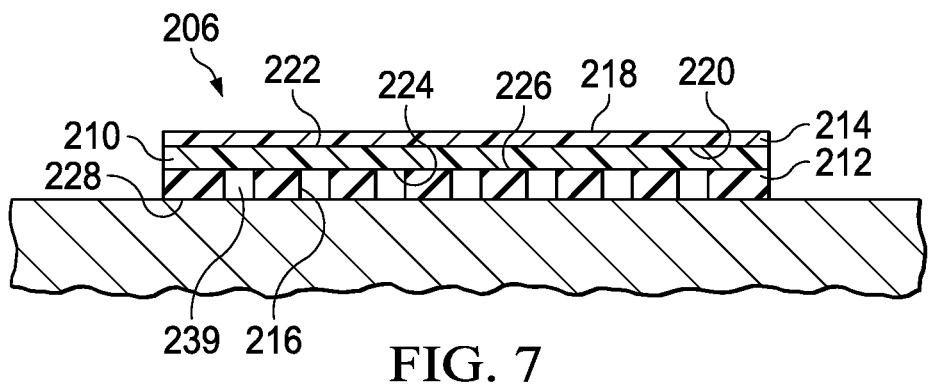
FIG. 7 is a sectional view illustrating additional details that may be associated with the cover of FIG. 6.

FIG. 7 is a sectional view of the cover 206 illustrating additional details that may be associated with some embodiments. If the support layer 211 is removed, the first adhesive layer 210 may be coupled directly to the second adhesive layer 212 to produce the cover 206. The cover 206 may be used as described above with respect to the cover 106 in FIG. 4A and FIG. 4B.

Figure 8A:
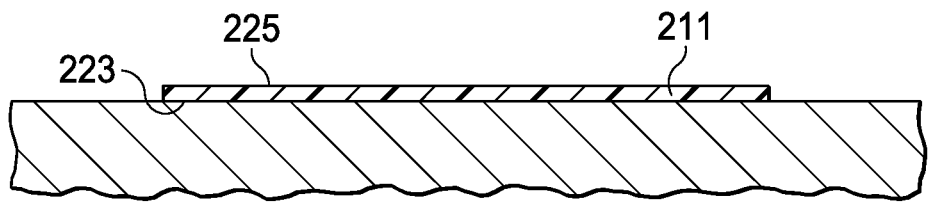
FIGS. 8A-8G are schematic views illustrating additional details that may be associated with an assembly process of the cover of FIG. 6.

The cover 206 can be manufactured without the use of a scrim layer. The operations can be performed using manufacturing processes and equipment to manipulate the materials as described below. FIG. 8A is a schematic view illustrating additional details that may be associated with some embodiments of the manufacturing process of the cover 206. In some embodiments, the support layer 211 may be provided and suitably disposed so that the first side 223 is supported by a suitable surface, and the second side 225 is exposed.

Figure 8B:
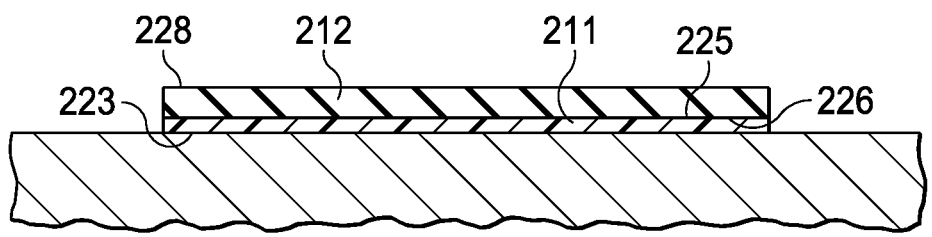

FIG. 8B is a schematic view illustrating additional details that may be associated with some embodiments of the manufacturing process of the cover 206. A sealing adhesive may be cast onto the second side 225 of the support layer 211. In some embodiments, the sealing adhesive may be cured or otherwise cross-linked to form the second adhesive layer 212 and couple the second adhesive layer 212 to the second side 225 of the support layer 211. In some embodiments, the sealing adhesive of the second adhesive layer 212 may be a two-part silicone system, such as those provided by Wacker, Dow, or NuSil. To cure, the two-part silicone system may be heated once applied to the second side 225 of the support layer 211. Heating may cause crosslinking or curing to cause the two-part silicone system to form a gel. In other embodiments, the sealing adhesive may be a one-part silicone system, and the sealing adhesive may be cured or crosslinked by exposing the one-part silicone system to ultraviolet light or ionizing radiation.

In other embodiments, the support layer 211 may be laminated to the second adhesive layer 212. For example, the sealing adhesive of the second adhesive layer 212 may be cast and cured as described above. After the sealing adhesive has cured to form the second adhesive layer 212, the support layer 211 may be laminated to the second adhesive layer 212.

Figure 8C:
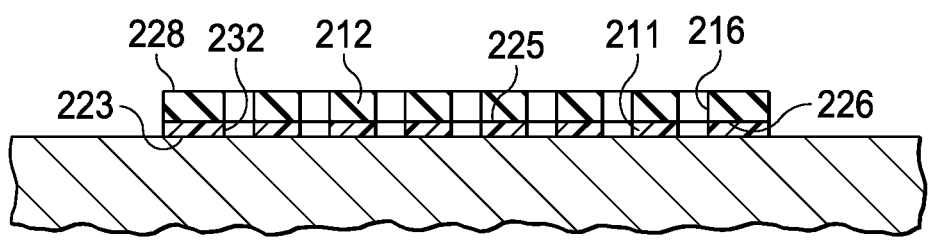

FIG. 8C is a schematic view illustrating additional details that may be associated with some embodiments of the manufacturing process of the cover 206. The plurality of apertures 216 and the plurality of apertures 232 may be formed following casting of the second adhesive layer 212 onto the support layer 211. In some embodiments, the apertures 216 and the apertures 232 may be formed using shaped pins that puncture the support layer 211 and the second adhesive layer 212 as the support layer 211 and the second adhesive layer 212 move along a manufacturing path. In other embodiments, the apertures 216 and the apertures 232 may be formed by rolling a drum having shaped pins along the support layer 211 and the second adhesive layer 212. The shaped pins may be configured to make the desired shape and size of the apertures 216 and the apertures 232. In other embodiments, the apertures 216 and the apertures 232 may be cut or torn. For example, a punch may be used to puncture the support layer 211 and the second adhesive layer 212. The apertures 216 and the apertures 232 may also be formed by melting portions of the support layer 211 and the second adhesive layer 212. For example, a heated element, such as a poker may be applied to the support layer 211 and the second adhesive layer 212, melting portions of the support layer 211 and the second adhesive layer 212. In some embodiments, the apertures 216 and the apertures 232 may be formed in the second adhesive layer 212 and the support layer 211, respectively, prior to the coupling of the support layer 211 and the second adhesive layer 212.

In some embodiments, a mold may be used to form the second adhesive layer 212. For example, the sealing adhesive may be cast into a mold having projections that extend into the sealing adhesive. After the sealing adhesive is cured, the mold and projections may be removed, leaving the apertures 216 formed in the second adhesive layer 212. The support layer 211 may then be laminated to the second adhesive layer 212. In some embodiments, the support layer 211 may not include the plurality of apertures 232.

Figure 8D:
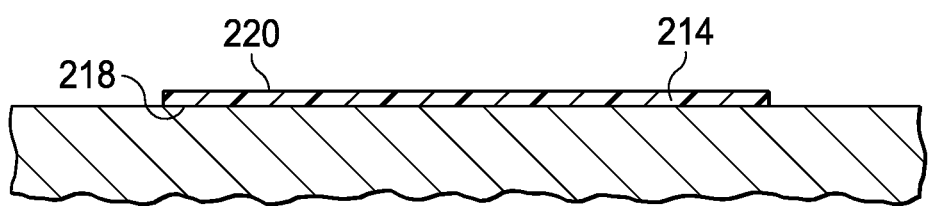

FIG. 8D is a schematic view illustrating additional details that may be associated with some embodiments of the manufacturing process of the cover 206. For example, the film layer 214 may be provided and positioned so that the first side 218 is supported by a suitable surface and the second side 220 is exposed.

Figure 8E:
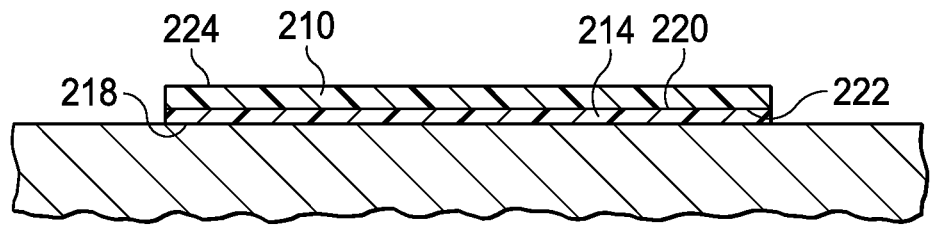

FIG. 8E is a schematic view illustrating additional details that may be associated with some embodiments of the manufacturing process of the cover 206. As illustrated in the example of FIG. 8E, the first adhesive layer 210 may be cast onto the second side 220 of the film layer 214 of FIG. 8D. In other embodiments, the first adhesive layer 210 may be cast and cured and the film layer 214 may then be laminated to the first adhesive layer 210.

Figure 8F:
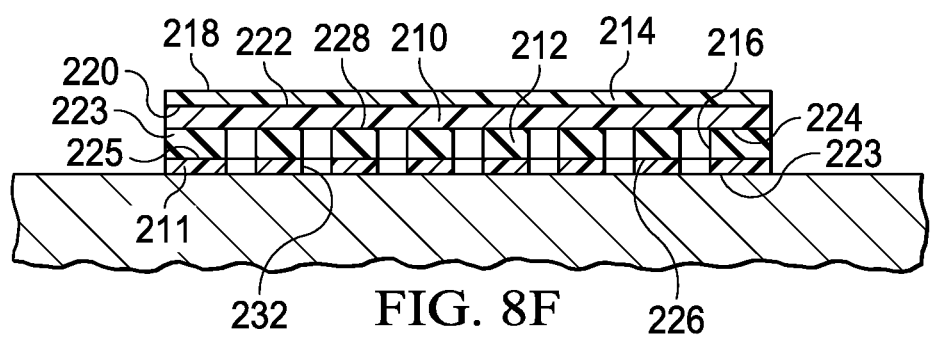

FIG. 8F is a schematic view illustrating additional details that may be associated with some embodiments of the manufacturing process of the cover 206. Following a curing or crosslinking process, the second adhesive layer 212 and the support layer 211 may be positioned so that the first side 223 of the support layer 211 is in contact with a surface, leaving the second side 228 of the second adhesive layer 212 free. The second side 224 of the first adhesive layer 210 of FIG. 8E may be brought proximate to the second side 228 of the second adhesive layer 212. The second side 224 of the first adhesive layer 210 may then be coupled to the second side 228 of the second adhesive layer 212, as illustrated in the example of FIG. 8F, forming one embodiment of the cover 206.

Figure 8G:
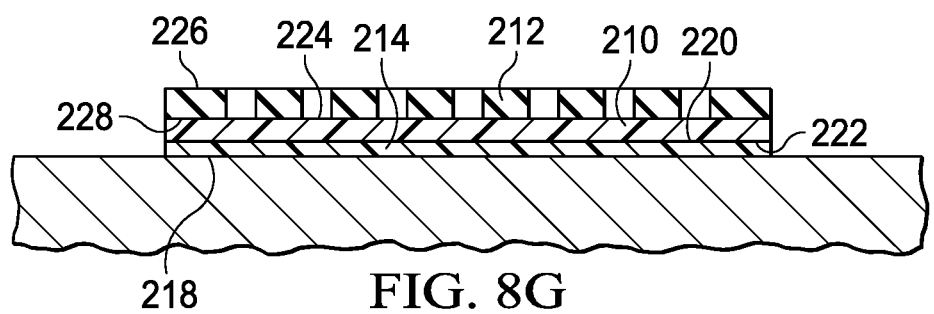

FIG. 8G is a schematic view illustrating additional details that may be associated with some embodiments of the manufacturing process of the cover 206. After coupling of the second side 224 of the first adhesive layer 210 to the second side 228 of the second adhesive layer 212 in the example of FIG. 8F, the cover 206 may be repositioned so that the first side 223 of the support layer 211 is exposed. The support layer 211 may then be removed from the first side 226 of the second adhesive layer 212.

Figure 9A:
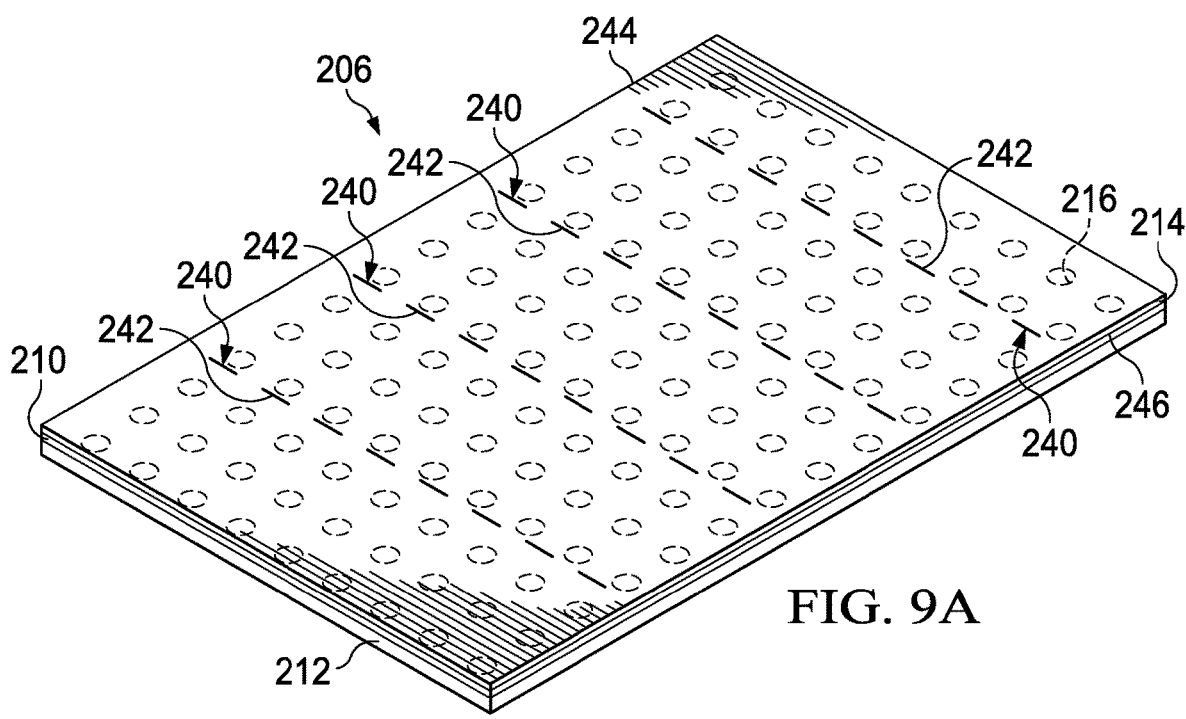
FIG. 9A is a perspective view illustrating additional details that may be associated with another cover that may be used with the therapy system of FIG. 1.

FIG. 9A is a perspective view of the cover 206, illustrating additional details that may be associated with some embodiments. The cover 206 includes the film layer 214, the first adhesive layer 210 coupled to the film layer 214, and the second adhesive layer 212 having the apertures 216 coupled to the first adhesive layer 210. In some embodiments, the cover 206 may include one or more sizing lines 240. Each sizing line 240 may extend across the cover 206 from a first edge 244 to a second edge 246. In some embodiments, the sizing lines 240 may be equidistantly spaced across the cover 206. For example, each sizing line 240 may be between about 5 centimeters and about 30 centimeters from adjacent sizing lines 240. In other embodiments, each sizing line 240 may be about 28 centimeters from adjacent sizing lines 240.

A sizing line 240 may be a weakened portion of the cover 206 that facilitates separation of a first portion of the cover 206 from a second portion of the cover 206. In some embodiments, each sizing line 240 may be formed by perforating the cover 206. For example, each sizing line 240 may have a plurality of perforations 242. In some embodiments, each perforation 242 may be between about 25 mm and about 60 mm from adjacent perforations 242 in the same sizing line 240. While each sizing line 240 is shown in portions of the cover 206 between apertures 216, in other embodiments, the sizing lines 240 may pass through the apertures 216.

Figure 9B:
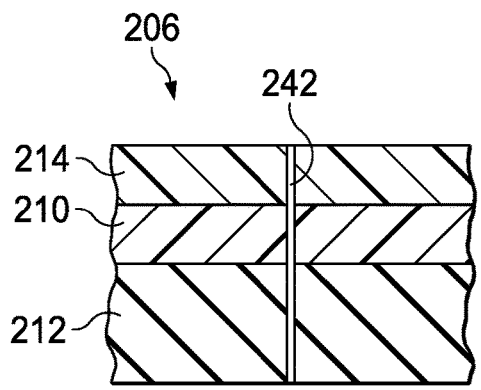
FIG. 9B is a sectional view illustrating additional details that may be associated with the cover of FIG. 9A.

FIG. 9B is a schematic view of the cover 206, illustrating additional details that may be associated with some embodiments of the perforations 242. As shown in FIG. 9B, each perforation 242 may be formed in the cover 206 that extends through the film layer 214, the first adhesive layer 210, and the second adhesive layer 212. If the cover 206 is applied to a tissue site and a sizing line 240 extends across the sealed therapeutic environment, the sealing adhesive of the second adhesive layer 212 may expand and fill the perforation 242 to seal the cover 206.

Figure 9C:
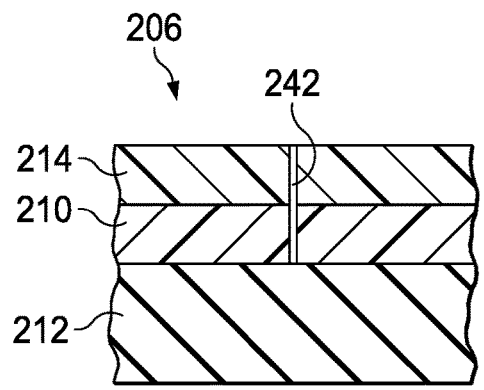
FIG. 9C is a sectional view illustrating additional details that may be associated with the cover of FIG. 9C.

FIG. 9C is a sectional view of the cover 206, illustrating additional details that may be associated with some embodiments of the perforations 242. As shown in FIG. 9C, each perforation 242 may be formed in the cover 206 that extends through the film layer 214 and the first adhesive layer 210, but not the second adhesive layer 212. The cover 206 may be torn along the sizing line 240 to separate portions of the cover 206.

Figure 10:
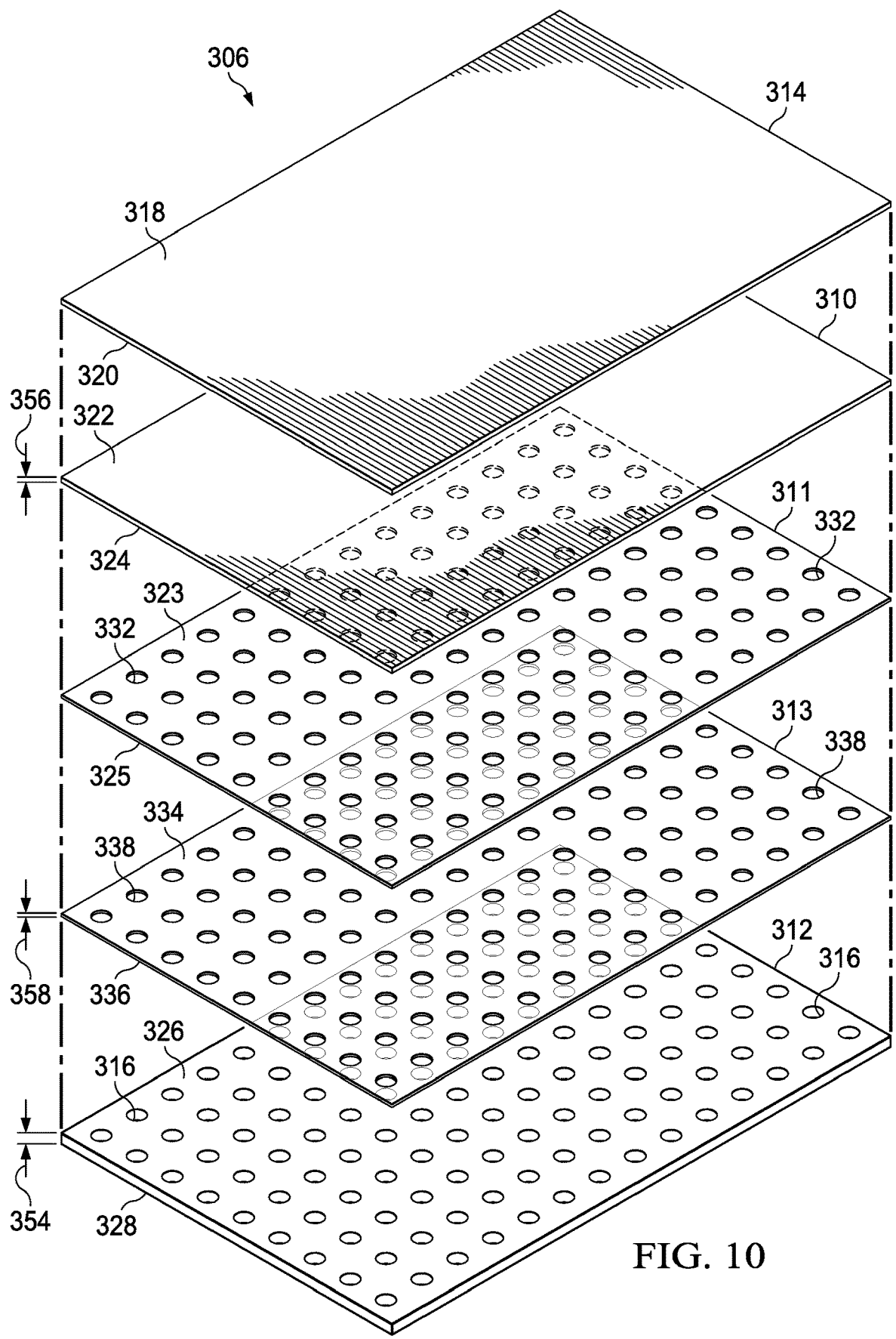
FIG. 10 is a perspective exploded view of another cover that can be used with the therapy system of FIG. 1.

FIG. 10 is a perspective exploded view of an example embodiment of a cover 306 that can be used with the therapy system 100. The cover 306 may include a first adhesive layer 310, a support layer 311, a second adhesive layer 312, and a film layer 314. The first adhesive layer 310, the support layer 311, the second adhesive layer 312, and the film layer 314 may be similar to and operate as described above with respect to the first adhesive layer 110, the support layer 111, the second adhesive layer 112, and the film layer 114.

The film layer 314 may have a first side 318 and a second side 320. The first adhesive layer 310 may also have a first side 322 and a second side 324. The first side 322 of the first adhesive layer 310 may face the second side 320 of the film layer 314. The first adhesive layer 310 may have a thickness 356, and in some embodiments, the thickness 356 of the first adhesive layer 310 may be about 30 microns to about 60 microns. In some embodiments, the first adhesive layer 310 may be coupled to the film layer 314.

The support layer 311 may have a first side 323 and a second side 325. In some embodiments, the support layer 311 may have a plurality of apertures 332. Each aperture 332 of the plurality of apertures 332 may extend through the support layer 311 from the first side 323 to the second side 325. In some embodiments, the support layer 311 may have a thickness of about 15 microns. The first side 323 of the support layer 311 may also have a substantially smooth surface.

The cover 306 may also include a third adhesive layer 313. The third adhesive layer 313 may be disposed between the support layer 311 and the second adhesive layer 312. The third adhesive layer 313 may have a first side 334 and a second side 336. The first side 334 of the third adhesive layer 313 may face the second side 325 of the support layer 311. In some embodiments, the third adhesive layer 313 may have a plurality of apertures 338 that extend through the third adhesive layer 313 from the first side 334 to the second side 336. The third adhesive layer 313 may be an acrylic adhesive having a coating weight between 25-65 grams per square meter (g.s.m.). In some embodiments, the third adhesive layer 313 may have a thickness 358. The thickness 358 of the third adhesive layer 313 may be between about 30 microns and about 60 microns. In other embodiments, the thickness 358 of the third adhesive layer 313 may be between about 15 microns and about 25 microns. Thicker adhesives, or combinations of adhesives, may be applied in some embodiments to improve the seal and reduce leaks.

Other example embodiments of the third adhesive layer 313 may include a double-sided tape, paste, hydrocolloid, hydrogel, silicone gel, or organogel.

The second adhesive layer 312 may have a first side 326 and a second side 328. The first side 326 of the second adhesive layer 312 may face the second side 336 of the third adhesive layer 313 and have a thickness 354. In some embodiments, the second adhesive layer 312 may have a plurality of apertures 316 that extend through the second adhesive layer 312 from the first side 326 to the second side 328.

The plurality of apertures 332, 338, 316 may be numerous shapes, including without limitation, circles, squares, stars, ovals, polygons, slits complex curves, rectilinear shapes, or triangles. Each aperture 332, 338, 316 of the plurality of apertures 332, 338, 316 may have an effective diameter. The average effective diameter is typically in the range of about 4 mm to about 50 mm. The plurality of apertures 332, 338, 316 may have a uniform pattern or may be randomly distributed on the support layer 311, the third adhesive layer 313, and the second adhesive layer 312, respectively. In some embodiments, the apertures 332, 338, 316 may be distributed so that centers of adjacent apertures 332, 338, 316 may be separated by between about 5 mm and about 100 mm. In other embodiments, the apertures 332, 338, 316 may be distributed so that the centers of adjacent apertures 332, 338, 316 may be separated by about 10 mm.

Regardless of the shape of the plurality of apertures 332, 338, 316, the plurality of apertures 332, 338, 316 in the support layer 311, the third adhesive layer 313, and the second adhesive layer 312, respectively, may leave void spaces in the support layer 311, the third adhesive layer 313, and the second adhesive layer 312, respectively. The percentage of void space of the plurality of apertures 332, 338, 316 may be equal to the percentage of the volume or surface area of the void spaces created by the plurality of apertures 332, 338, 316 to the total volume or surface area of the support layer 311, the third adhesive layer 313, and the second adhesive layer 312, respectively. In some embodiments, the percentage of void space may be between about 40% and about 75%. In other embodiments, the percentage of void space may be about 55%. The organization of the plurality of apertures 332, 338, 316 can also impact the percentage of void space. The plurality of apertures 332, 338, 316 may be formed by punching, cutting, melting, or drilling the support layer 311, the third adhesive layer 313, and the second adhesive layer 312, respectively.

To manufacture the cover 306, the third adhesive layer 313 may be coupled to the support layer 311, and the second adhesive layer 312 may be coupled to the third adhesive layer 313 to form a first assembly. The apertures 332, 338, and 316 may be formed in the first assembly. The first adhesive layer 310 may be coupled to the film layer 314 to form a second assembly. The first assembly and the second assembly may be coupled to each other so that the support layer 311 is coupled to the first adhesive layer 310.

In some embodiments, the first adhesive layer 310 and the third adhesive layer 313 may be formed from a material having a substantially similar composition. For example, the first adhesive layer 310 and the third adhesive layer 313 may be formed from the same acrylic adhesive. If the first adhesive layer 310 and the third adhesive layer 313 are formed from the same acrylic adhesive, the first adhesive layer 310 and the third adhesive layer 313 may react similarly in response to outside stimuli, such as the passage of time and exposure to heat. In some embodiments, the first adhesive layer 310 and the third adhesive layer 313 may expand and/or contract at substantially the same rate in response to the same stimuli. By forming the first adhesive layer 310 and the third adhesive layer 313 from the same material, the cover 306 can reduce instances of acrylic adhesive exposure about a perimeter of the cover 306 compared to covers using dissimilar acrylic adhesives to form the first adhesive layer 310 and the third adhesive layer 313.

In some embodiments, the first side 323 or the second side 325 of the support layer 311 may include printing. For example, the first side 323 of the support layer 311 may be marked with a manufacturer's brand or trademark. In other examples, information regarding suggested uses for the cover 306 may be printed on the first side 323 of the support layer 311. The printing may be visible through the first adhesive layer 310 and the film layer 314 during use of the cover 306. Because the support layer 311 is covered by the first adhesive layer 310 and the film layer 314, the printing is less susceptible to washing off during use than if the printing is applied to the film layer 314. For example, if fluid, including liquid, comes into contact with the film layer 314, it will not come into contact with the support layer 311 or printing formed on the support layer 311.

Figure 11:
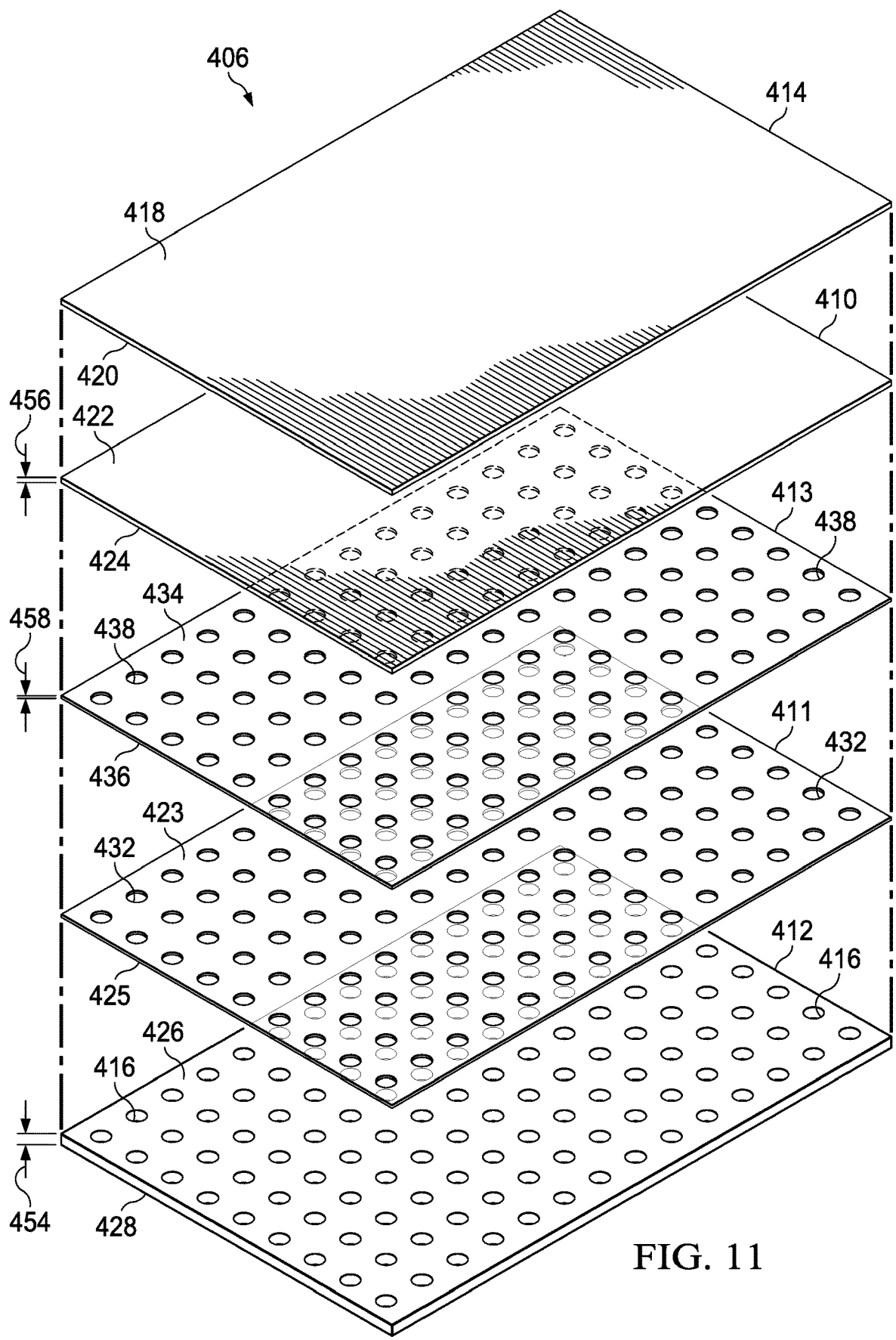
FIG. 11 is a perspective exploded view of another cover that can be used with the therapy system of FIG. 1.

FIG. 11 is a perspective exploded view of an example embodiment of a cover 406 that can be used with the therapy system 100. The cover 406 may include a first adhesive layer 410, a support layer 411, a second adhesive layer 412, a third adhesive layer 413, and a film layer 414. The first adhesive layer 410, the support layer 411, the second adhesive layer 412, and the film layer 414 may be similar to and operate as described above with respect to the first adhesive layer 110, the support layer 111, the second adhesive layer 112, and the film layer 114.

The film layer 414 may have a first side 418 and a second side 420. The first adhesive layer 410 may also have a first side 422 and a second side 424. The first side 422 of the first adhesive layer 410 may face the second side 420 of the film layer 414. The first adhesive layer 410 may have a thickness 456, and in some embodiments, the thickness 456 of the first adhesive layer 410 may be between about 40 microns and about 60 microns. In some embodiments, the first adhesive layer 410 may be coupled to the film layer 414.

The support layer 411 may have a first side 423 and a second side 425. In some embodiments, the support layer 411 may have a plurality of apertures 432. Each aperture 432 of the plurality of apertures 432 may extend through the support layer 411 from the first side 423 to the second side 425. The third adhesive layer 413 may be disposed between the support layer 411 and the first adhesive layer 410. The third adhesive layer 413 may have a first side 434 and a second side 436. The first side 434 of the third adhesive layer 413 may face the second side 424 of the first adhesive layer 410. The second side 436 of the third adhesive layer 413 may face first side 423 of the support layer 411. In some embodiments, the third adhesive layer 413 may have a plurality of apertures 438 that extend through the third adhesive layer 413 from the first side 434 to the second side 436. The third adhesive layer 413 may be an acrylic adhesive having a coating weight between 25-65 grams per square meter (g.s.m.). In some embodiments, the third adhesive layer 413 may have a thickness 458. The thickness 458 of the third adhesive layer 413 may be between about 15 microns and about 25 microns. Thicker adhesives, or combinations of adhesives, may be applied in some embodiments to improve the seal and reduce leaks. Other example embodiments of the third adhesive layer 413 may include a double-sided tape, paste, hydrocolloid, hydrogel, silicone gel, or organogel.

The second adhesive layer 412 may have a first side 426 and a second side 428. The first side 426 of the second adhesive layer 412 may face the second side 425 of the support layer 411 and have a thickness 454. In some embodiments, the second adhesive layer 412 may have a plurality of apertures 416 that extend through the second adhesive layer 412 from the first side 426 to the second side 428.

The plurality of apertures 438, 432, 416 may be numerous shapes, including without limitation, circles, squares, stars, ovals, polygons, slits complex curves, rectilinear shapes, or triangles. Each aperture 438, 432, 416 of the plurality of apertures 438, 432, 416 may have an effective diameter. The average effective diameter is typically in the range of about 4 mm to about 50 mm. The plurality of apertures 438, 432, 416 may have a uniform pattern or may be randomly distributed on the support layer 411, the third adhesive layer 413, and the second adhesive layer 412, respectively. In some embodiments, the apertures 438, 432, 416 may be distributed so that centers of adjacent apertures 438, 432, 416 may be separated by between about 5 mm and about 100 mm. In other embodiments, the apertures 438, 432, 416 may be distributed so that the centers of adjacent apertures 438, 432, 416 may be separated by about 10 mm.

Regardless of the shape of the plurality of apertures 438, 432, 416, the plurality of apertures 438, 432, 416 in the third adhesive layer 413, the support layer 411, and the second adhesive layer 412, respectively, may leave void spaces in the third adhesive layer 413, the support layer 411, and the second adhesive layer 412, respectively. The percentage of void space of the plurality of apertures 438, 432, 416 may be equal to the percentage of the volume or surface area of the void spaces created by the plurality of apertures 438, 432, 416 to the total volume or surface area of the third adhesive layer 413, the support layer 411, and the second adhesive layer 412, respectively. In some embodiments, the percentage of void space may be between about 40% and about 75%. In other embodiments, the percentage of void space may be about 55%. The organization of the plurality of apertures 438, 432, 416 can also impact the percentage of void space. The plurality of apertures 438, 432, 416 may be formed by punching, cutting, melting, or drilling the third adhesive layer 413, the support layer 411, and the second adhesive layer 412, respectively.

Figure 12A:
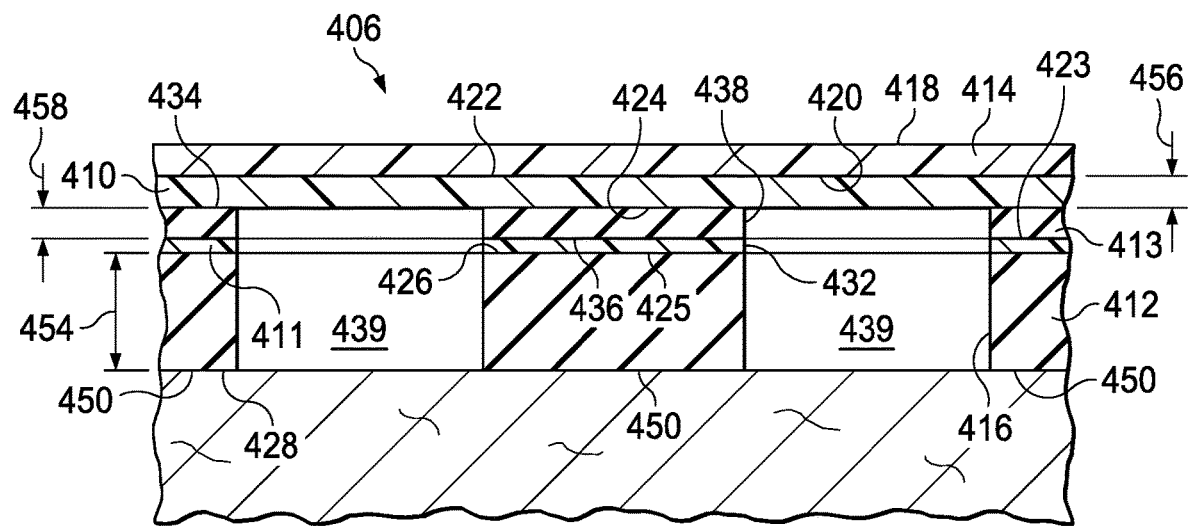
FIG. 12A is a sectional view of the cover of FIG. 11 illustrating additional details that may be associated with the cover in a first position.

FIG. 12A is a schematic view of the assembled cover 406 in a first position on the epidermis, illustrating additional details that may be associated with some embodiments. The second side 420 of the film layer 414 may be coupled to first side 422 of the first adhesive layer 410. The second side 424 of the first adhesive layer 410 may be coupled to the first side 434 of the third adhesive layer 413. The second side 436 of the third adhesive layer 413 may be coupled to the first side 423 of the support layer 411. And the second side 425 of the support layer 411 may be coupled to the first side 426 of the second adhesive layer 412. The cover 406 may be disposed over the epidermis to form the sealed therapeutic environment. The tackiness of the sealing adhesive of the second adhesive layer 412 may form sealing couplings 450 between the second side 428 of the second adhesive layer 412 and the epidermis to hold the cover 406 in an initial position as illustrated in FIG. 12A. The tackiness of the sealing adhesive of the second adhesive layer 412 may be such that the cover 406 may be removed and reapplied or repositioned. In some embodiments, the thickness 454 of the second adhesive layer 412 may prevent the first adhesive layer 410 from contacting the epidermis, forming a gap 439 between the first adhesive layer 410 and the epidermis. In some embodiments, sidewalls of the gap 439 comprise the aperture 416 of the second adhesive layer 412, the aperture 432 of the support layer 411, and the aperture 438 of the third adhesive layer 413.

Figure 12B:
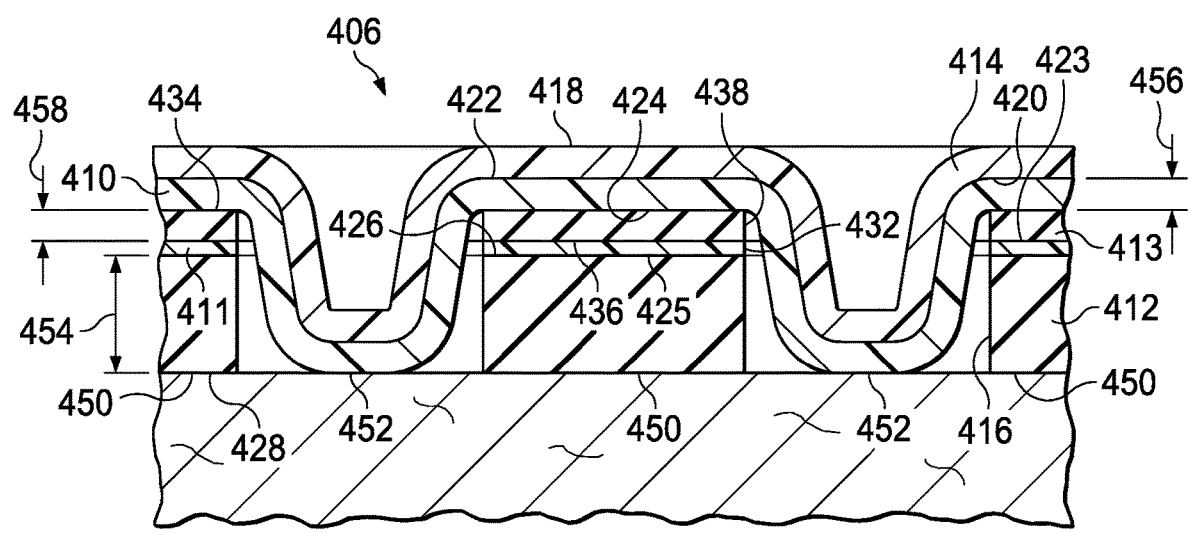
FIG. 12B is a sectional view of the cover of FIG. 11 illustrating additional details that may be associated with the cover in a second position.

FIG. 12B is a schematic view of the cover 406 in a second position, illustrating additional details that may be associated with some embodiments. If the cover 406 is placed at a tissue site, a force may be applied to the first side 418 of the film layer 414. The force may cause at least some portion of the bonding adhesive of the first adhesive layer 410 to move through the apertures 438, the apertures 432, and the apertures 416. In response, the second side 424 of the first adhesive layer 410 may contact the epidermis and form bonding couplings 452, as illustrated in the second position of FIG. 12B. For example, the bonding couplings 452 may be located where the second side 424 of the first adhesive layer 410 adheres to the epidermis. In some embodiments, the bonding couplings 452 may have a peel force against the epidermis between about 0.5 N/25 mm and about 9.5 N/25 mm.

The average effective diameter of the apertures 438, the apertures 432, and the apertures 416 may be varied as one control of the tackiness or adhesion strength of the cover 406. Generally, the strength of the bond of the bonding coupling 452 is proportional to the effective diameter of the apertures 438, the apertures 432, and the apertures 416; the thickness 454 of the second adhesive layer 412, the thickness of the support layer 411, and the thickness 458 of the third adhesive layer 413; and the tackiness of the first adhesive layer 410. The more of the first adhesive layer 410 that extends through the across the gap 439, the more bonding adhesive of the first adhesive layer 410 contacts the epidermis and the stronger the bond of the bonding coupling 452. In some embodiments, the thickness 454 of the second adhesive layer 412, the thickness of the support layer 411, and the thickness 458 of the third adhesive layer 413 may permit more of the first adhesive layer 410 to extend across the gap 439 and increase the bond of the bonding coupling 452.

As an example of the interplay, if a first bonding adhesive is used to form the first adhesive layer 410 and the thickness 454 of the second adhesive layer 412, the support layer 411, and the thickness 458 of the third adhesive layer 413 is collectively a first thickness, the average effective diameter of the apertures 438, the apertures 432, and the apertures 416 may be a first effective diameter so that the bonding couplings 452 have a first bond strength. If the thickness 454 of the second adhesive layer 412, the thickness of the support layer 411, and the thickness 458 of the third adhesive layer 413 is collectively increased to be larger than the first thickness, the average effective diameter of the apertures 438, the apertures 432, and the apertures 416 may increase to be larger than the first effective diameter to achieve the first bond strength of the bonding coupling 452. In some embodiments, the thickness 454 may be about 250 microns, the first adhesive layer 410 may be about 30 microns with a bonding adhesive having a tackiness of about 9.5 N/25 mm wide strip, and the average effective diameter of each aperture 416 of the plurality of apertures 416 may be about 7 mm.

Figure 13A:
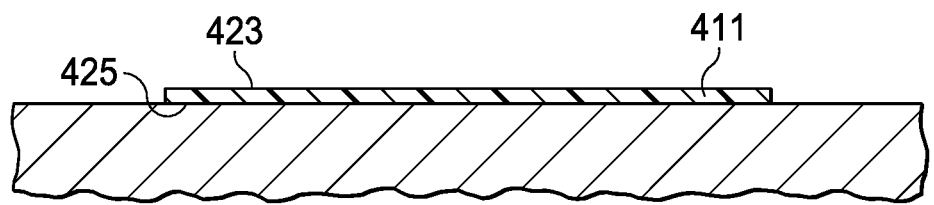
FIGS. 13A-13G are schematic views illustrating additional details that may be associated with an assembly process of the cover of FIG. 11.

The cover 406 can be manufactured in many ways including by following the operations provided below to produce the cover 406 without a scrim layer. The operations can be performed using manufacturing processes and equipment to manipulate the materials as describe below. FIG. 13A is a schematic view illustrating additional details that may be associated with some embodiments of the manufacturing process of the cover 406. In some embodiments, the support layer 411 may be provided and suitably disposed so that the second side 425 is supported by a suitable surface, and the first side 423 is exposed.

Figure 13B:
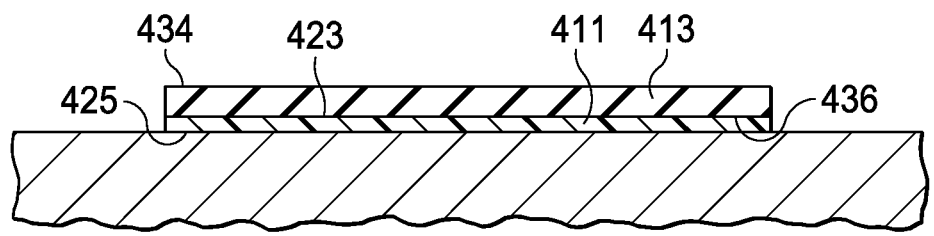

FIG. 13B is a schematic view illustrating additional details that may be associated with some embodiments of the manufacturing process of the cover 406. The third adhesive layer 413 may be cast onto the first side 423 of the support layer 411. In other embodiments, the third adhesive layer 413 may be cast and cured, and the support layer 411 may be laminated to the third adhesive layer 413.

Figure 13C:
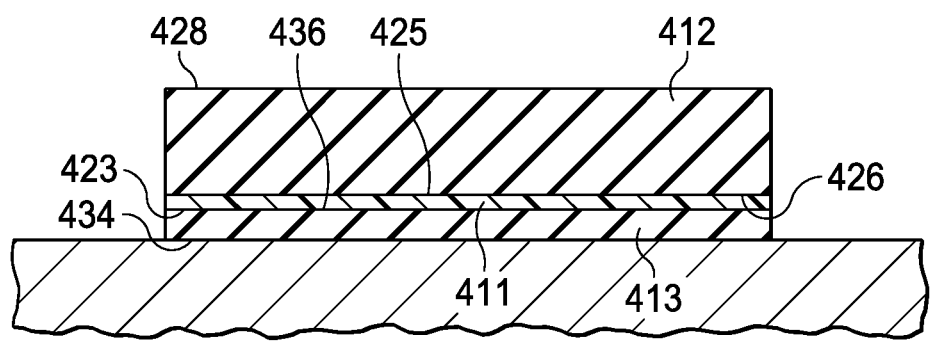

FIG. 13C is a schematic view illustrating additional details that may be associated with some embodiments of the manufacturing process of the cover 406. The support layer 411 and the third adhesive layer 413 may be oriented so that the first side 434 of the third adhesive layer 413 is supported by a suitable surface, and the second side 425 of the support layer 411 is exposed. A sealing adhesive may be cast onto the second side 425 of the support layer 411. In some embodiments, the sealing adhesive may be cured or otherwise cross-linked to form the second adhesive layer 412 and couple the second adhesive layer 412 to the second side 425 of the support layer 411. In some embodiments, the sealing adhesive of the second adhesive layer 412 may be a two-part silicone system, such as those provided by Wacker, Dow, or NuSil. To cure, the two-part silicone system may be heated once applied to the second side 425 of the support layer 411. Heating may cause cross-linking or curing to cause the two-part silicone system to form a gel. In other embodiments, the sealing adhesive may be a one-part silicone system, and the sealing adhesive may be cured or cross-linked by exposing the one-part silicone system to ultraviolet light or ionizing radiation.

In other embodiments, the support layer 411 may be laminated to the second adhesive layer 412. For example, the sealing adhesive of the second adhesive layer 412 may be cast and cured as described above. After the sealing adhesive has cured to form the second adhesive layer 412, the support layer 411 may be laminated to the second adhesive layer 412.

Figure 13D:
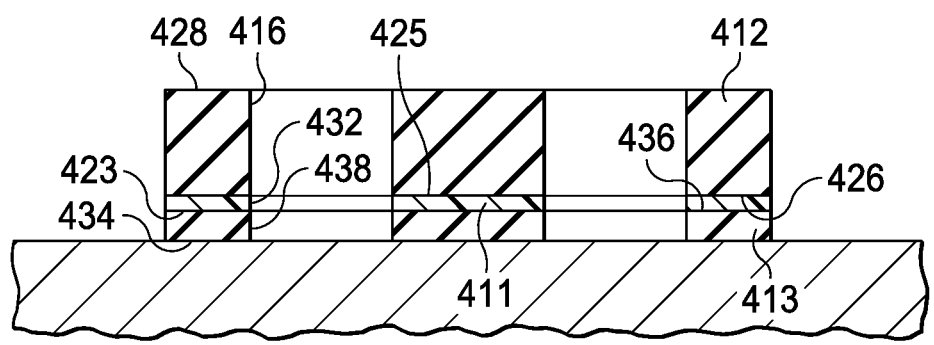

FIG. 13D is a schematic view illustrating additional details that may be associated with some embodiments of the manufacturing process of the cover 406. The plurality of apertures 416, the plurality of apertures 432, and the plurality of apertures 438 may be formed following casting of the second adhesive layer 412 and the third adhesive layer 413 onto the support layer 411. In some embodiments, the plurality of apertures 416, the plurality of apertures 432, and the plurality of apertures 438 may be formed using shaped pins that puncture the support layer 411, the second adhesive layer 412, and the third adhesive layer 413 as the support layer 411, the second adhesive layer 412, and the third adhesive layer 413 move along a manufacturing path. In other embodiments, the plurality of apertures 416, the plurality of apertures 432, and the plurality of apertures 438 may be formed by rolling a drum having shaped pins along the support layer 411, the second adhesive layer 412, and the third adhesive layer 413. The shaped pins may be configured to make the desired shape and size of the plurality of apertures 416, the plurality of apertures 432, and the plurality of apertures 438. In other embodiments, the plurality of apertures 416, the plurality of apertures 432, and the plurality of apertures 438 may be cut or torn. For example, a punch may be used to puncture the support layer 411, the second adhesive layer 412, and the third adhesive layer 413. The plurality of apertures 416, the plurality of apertures 432, and the plurality of apertures 438 may also be formed by melting portions of the support layer 411, the second adhesive layer 412, and the third adhesive layer 413. For example, a heated element, such as a poker may be applied to the support layer 411, the second adhesive layer 412, and the third adhesive layer 413, melting portions of the support layer 411, the second adhesive layer 412, and the third adhesive layer 413. In some embodiments, the plurality of apertures 416, the plurality of apertures 432, and the plurality of apertures 438 may be formed in the second adhesive layer 412, the support layer 411, and the third adhesive layer 413, respectively, prior to the coupling of the support layer 411, the second adhesive layer 412, and the third adhesive layer 413 to each other.

In some embodiments, a mold may be used to form the second adhesive layer 412. For example, the sealing adhesive may be cast into a mold having projections that extend into the sealing adhesive. After the sealing adhesive is cured, the mold and projections may be removed, leaving the apertures 416 formed in the second adhesive layer 412. The support layer 411 may then be laminated to the second adhesive layer 412. The third adhesive layer 413 may then be cast onto the first side 423 of the support layer 411. If the apertures 416 are formed with a mold, the apertures 432 and the apertures 438 may be separately formed in the support layer 411 and the third adhesive layer 413, respectively.

Figure 13E:
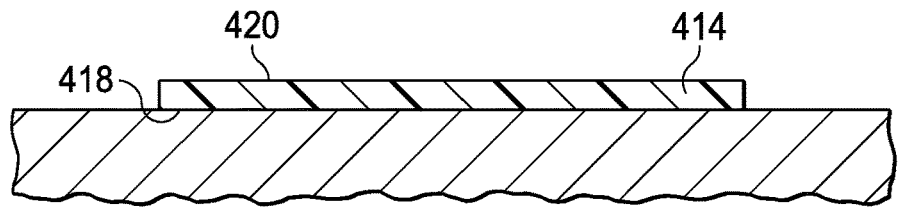

FIG. 13E is a schematic view illustrating additional details that may be associated with some embodiments of the manufacturing process of the cover 406. In the example embodiment of FIG. 13E, the film layer 414 may be provided and positioned so that the first side 418 is supported by a suitable surface and the second side 420 is exposed.

Figure 13F:
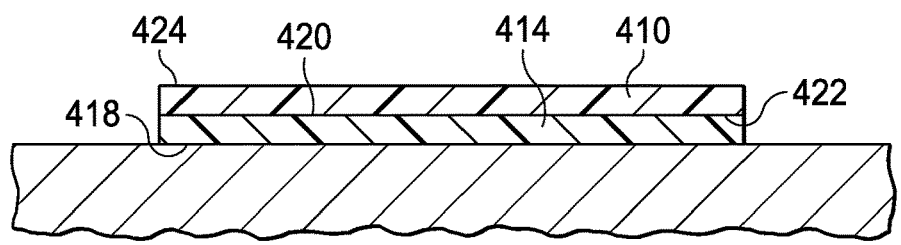

FIG. 13F is a schematic view illustrating additional details that may be associated with some embodiments of the manufacturing process of the cover 406. For example, the first adhesive layer 410 may be cast onto the second side 420 of the film layer 414 of FIG. 13E. In other embodiments, the first adhesive layer 410 may be cast and cured, and the film layer 414 may then be laminated to the first adhesive layer 410.

Figure 13G:
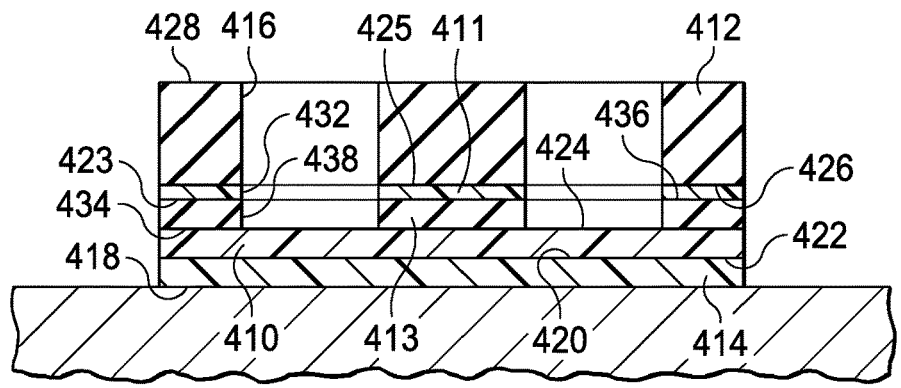

FIG. 13G is a schematic view illustrating additional details that may be associated with some embodiments of the manufacturing process of the cover 406. The support layer 411 and the second adhesive layer 412 may be positioned so that the first side 434 of the third adhesive layer 413 is proximate to the second side 424 of the first adhesive layer 410 of FIG. 13E. The first side 434 of the third adhesive layer 413 may be coupled to the second side 424 of the first adhesive layer 410 to form the cover 406 as shown in the example of FIG. 13G. In other embodiments, the second side 424 of the first adhesive layer 410 may be brought proximate to the first side 434 of the third adhesive layer 413. The second side 424 of the first adhesive layer 410 may then be coupled to the first side 434 of the third adhesive layer 413, forming the cover 406.

Figure 14:
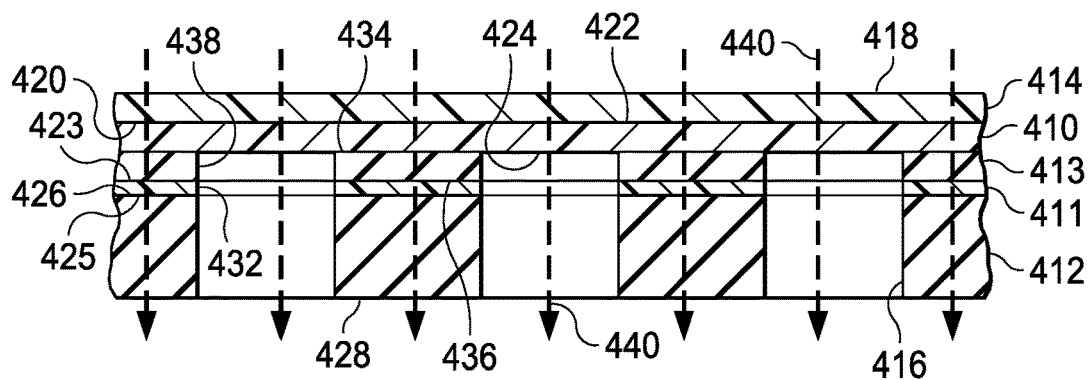
FIG. 14 is a sectional view of the cover of FIG. 11 illustrating additional details associated with light transmission through the cover.

FIG. 14 is a schematic view of the cover 406 illustrating additional details that may be associated with some embodiments. The cover 406 may be substantially transparent. For example, the cover 406 may have a low absorbance and transmit light through the cover 406 at a high rate. As shown in FIG. 14, light, as represented by arrows 440, may pass through the cover 406 unobstructed, having no physical barrier to prevent light penetration. As a result, light 440 may be reflected by objects to which the cover 406 is attached.

In some embodiments, the cover 106, the cover 206, the cover 306, and the cover 406 may be substantially transparent. For example, in some embodiments the transmittance of the cover 106, the cover 206, the cover 306, and the cover 406 for visible electro-magnetic radiation may be between about 70% and about 100%. In other embodiments, the transmittance of the cover 106, the cover 206, the cover 306, and the cover 406 for visible electro-magnetic radiation may be about 90%. Generally, transmittance may refer to the ratio of the amount of radiation passing through a surface to the amount of radiation falling on the surface. Materials and objects having a high transmittance, for example, approaching 1 or 100%, may be transparent. Factors that may impact the transmittance of the cover 106, the cover 206, the cover 306, and the cover 406 may include the amount of electromagnetic radiation the materials of the cover 106, the cover 206, the cover 306, and the cover 406 absorb, and the amount of the electro-magnetic radiation the materials of the cover 106, the cover 206, the cover 306, and the cover 406 scatter. By manufacturing the cover 106, the cover 206, the cover 306, and the cover 406 without a scrim layer, the amount of electro-magnetic radiation the materials of the cover absorb and scatter can be decreased compared to a cover having a scrim layer. The tendency of a material to absorb, scatter, or otherwise attenuate light can be referred to as absorbance. Manufacturing the cover 106, the cover 206, the cover 306, and the cover 406 without a scrim layer can increase the ability of the cover 106, the cover 206, the cover 306, and the cover 406 to transmit electro-magnetic radiation, i.e., decrease absorbance. For example, referring to FIG. 1, the transmittance of the cover 106 may permit the tissue interface 108 and the tissue site to be seen through the cover 106.

Figure 15:
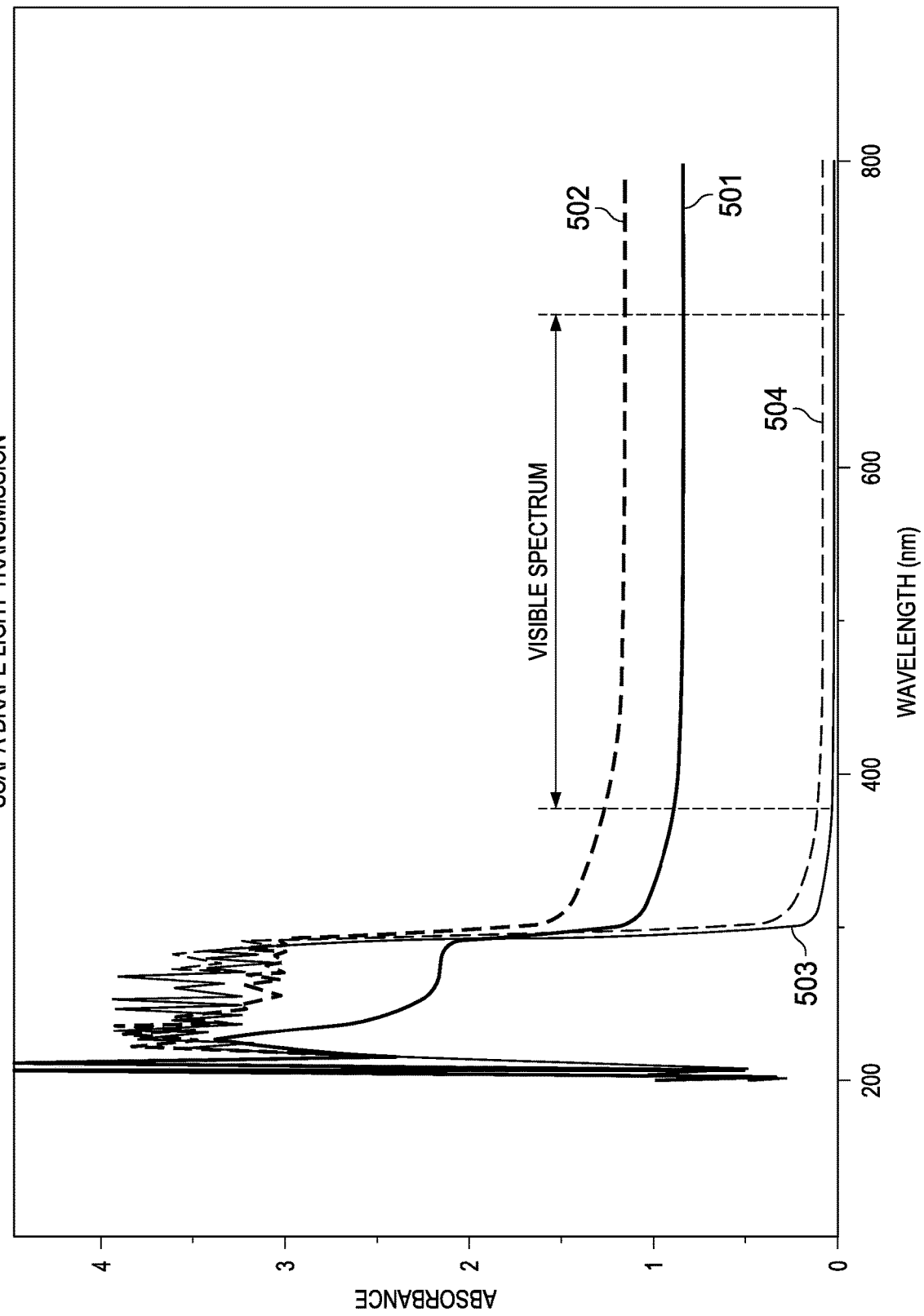
FIG. 15 is a graph of visible light absorption for various covers, including the cover of FIG. 11.

FIG. 15 is a graphical depiction of absorbance measured across covers, illustrating additional details that may be associated with some embodiments. In the example, covers having a scrim layer and covers having no scrim layer, such as the cover 406, were tested for absorbance. The testing apparatus included a substantially transparent surface having a light sensor on a first side and a light source on a second side. The light source was configured to produce a substantially white light, and the light sensor was configured to measure the transmittance through the transparent surface. The exemplary cover was placed on the second side of the transparent surface. The light source was turned on, and the transmittance through the cover was measured by the light sensor. Based on the measured transmittance, the absorbance was determined. Absorbance is a dimensionless measurement that reflects the amount of light absorbed and attenuated, which can include both light reflected and scattered. Generally, a higher absorbance indicates greater opaqueness of an object and lower absorbance indicates greater transparency.

A cover 501 having a polyurethane scrim layer formed from a silicone gel was tested for absorbance. A first side of the scrim layer was coated with a silicone adhesive, and a second side of the scrim layer was coated with an acrylic adhesive. The scrim layer, silicone adhesive, and acrylic adhesive was perforated. The perforated scrim layer, silicone adhesive, and acrylic adhesive was laminated to a polyurethane film also having an acrylic adhesive. The acrylic adhesive of the scrim layer was adhered to the acrylic adhesive of the polyurethane film. The polyurethane film had a thickness of about 40 microns, the acrylic adhesive had a thickness of about 50 microns, and the scrim layer had a thickness of about 50 microns. A coating weight of the silicone adhesive for the cover 501 was about 250 gsm. As shown in FIG. 15, the absorbance of the cover 501 showed variation for wavelengths less than about 300 nm. In the visible light spectrum between about 390 nm and about 700 nm, the absorbance of the cover 501 was about 1. An absorbance of about 1 indicates that approximately 10% of the light is transmitted through the cover 501 and about 90% of the light is attenuated by the cover 501. The cover 501 may be considered substantially opaque.

Another cover 502 was also tested for absorbance. The cover 502 was constructed as described above with respect to the cover 501. The cover 502 included a thicker silicone adhesive coated onto the scrim layer. For the cover 502, the coating weight of the silicone adhesive was about 500 gsm. As shown in FIG. 15, the cover 502 has an absorbance in the visible light spectrum (between about 390 nm and about 700 nm) of about 1.3, indicating that the cover 502 permitted less light transmission than the cover 501. The cover 502 may be considered substantially opaque.

Another cover 503 was also tested for absorbance. The cover 503 was constructed as described above with respect to the cover 406. For the cover 503, the film layer 414 had a thickness of about 25 microns, the first adhesive layer 410 had a coating weight of about 45 gsm, the third adhesive layer 413 had a coating weight of about 20 gsm, the support layer 411 had a thickness of about 15 microns, and the second adhesive layer 412 had a coating weight of about 150 gsm. As shown in FIG. 15, the cover 503 has an absorbance less than 1, and very close to 0, indicating that greater than about 80% of the light transmitted through the cover 503. In some embodiments, the absorbance of the cover 503 was less than about 0.1. The average absorbance of the cover 503 across the visible light spectrum between about 390 nm and about 700 nm was about 0.02. Similarly, a cover 504 was tested. The cover 504 is similar to the cover 503 as described above. For the cover 504, the second adhesive layer 412 had a coating weight of about 300 gsm. As shown in FIG. 15, the absorbance of the cover 504 is slightly greater than the cover 503. The average absorbance of the cover 504 across the visible spectrum from 390 nm to about 700 nm is about 0.07. Both the cover 503 and the cover 504 may be considered substantially transparent.

The cover 503 and the cover 504, produced as described above with respect to the cover 406, have substantially lower absorbance than covers, such as the cover 501 and the cover 502, that include a scrim layer. As a result, the cover 503 and the cover 504 are substantially transparent, permitting light to pass through the cover 503 and the cover 504 to be reflected by objects underneath the cover 503 and the cover 504. The transparency of the cover 503 and the cover 504 can permit a clinician to see color and other details of a tissue site. Color that can be perceived through an object, such as glass, is affected by the wavelengths of light that are absorbed and reflected by the object. For example, an object that appears visibly red may reflect electromagnetic radiation having wavelengths in the red spectrum while absorbing electromagnetic radiation having wavelengths of the non-red spectrum. In some embodiments, the absorbance of the cover 503 and the cover 504 is low, less than about 0.07, permitting a substantial portion of the electro-magnetic radiation in the visible spectrum to pass through the cover 503 and the cover 504. Consequently, the objects perceived through the cover 503 and the cover 504, such as a tissue site or the tissue interface 108, may have a same appearance as the object perceived independently of the cover 503 and the cover 504, i.e., as if nothing is between the clinician and the tissue site.

Figure 16:
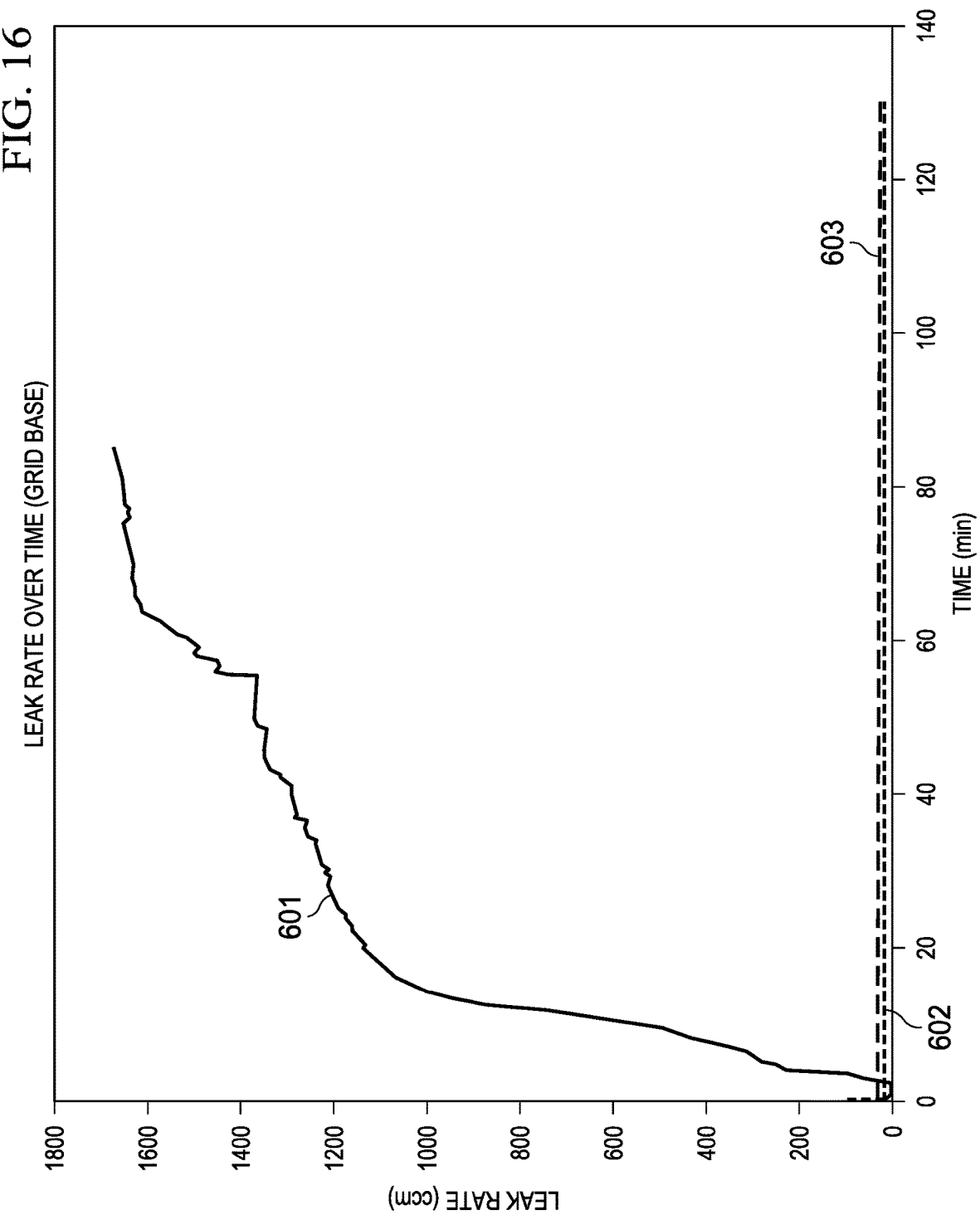
FIG. 16 is a graph of leak rate versus time for various covers, including the cover of FIG. 11.

FIG. 16 is a graphical depiction of leak rates for exemplary covers, illustrating additional details that may be associated with some embodiments. In the example, each cover was positioned on a testing apparatus having a grid of channels formed therein. The channels of the grid had a depth of approximately 150 microns, and each channel was spaced approximately 0.75 mm from adjacent channels. The covers were placed over the grid, and sealed to the surface of the grid. A negative-pressure therapy apparatus was fluidly coupled to an area between the cover and the grid, and negative-pressure therapy was conducted. During the test, a negative pressure of about 125 mmHg was maintained in the area between the cover and the grid. A leak rate of the cover was then calculated. The leak rate was determined based on the operation of the negative-pressure therapy apparatus to maintain the area under the cover at approximately 125 mmHg negative pressure. For example, the operation of the negative-pressure therapy apparatus was monitored. Based on a known flow rate for the negative-pressure therapy apparatus, the operational time of the negative-pressure therapy apparatus was measured to determine a total volume of fluid moved by the negative-pressure therapy apparatus during the operational time. From the total volume of fluid moved by the negative-pressure therapy apparatus for the operational time, the leak rate was calculated.

A first cover 601 was tested as described above to determine its leak rate. The cover 601 is similar to and includes the components of the cover 406. For the cover 601, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having a thickness of about 40 microns. The second adhesive layer 412 was formed from a silicone gel, such as a 6054 silicone gel produced by Scapa™, having a coating weight of about 150 gsm. And the third adhesive layer was formed from an acrylic adhesive having a coating weight of about 20 gsm. As shown in FIG. 16, the cover 601 exhibited an increasing leak rate over time. The initial leak rate was about 0 cubic centimeters per minute (ccm), and the leak rate increased to about 1600 ccm after approximately 90 minutes.

A cover 602 was also tested as described above to determine its leak rate. The cover 602 is similar to and includes the components of the cover 406. For the cover 602, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having a thickness of about 25 microns. The second adhesive layer 412 comprised a silicone gel, such as a RX1423s silicone gel produced by Scapa™, having a coating weight of about 150 gsm. The third adhesive layer comprises an acrylic adhesive having a coating weight of about 20 gsm. As shown in FIG. 16, the cover 602 maintained a low leak rate over time. For example, the initial leak rate was slightly greater than about 0 ccm, averaged about 23 ccm, and the leak rate was maintained for greater than 120 minutes.

A cover 603 was also tested as described above to determine its leak rate. The cover 603 is similar to and includes components of the cover 406; however, the cover 603 did not include the third adhesive layer 413. In the example, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having thickness of about 25 microns. The second adhesive layer 412 was formed from a polyurethane gel, such as a 9772B polyurethane gel produced by Scapa™ having a coating weight of about 200 gsm. As shown in FIG. 16, the cover 603 maintained a low leak rate over time as shown by line 603. The initial leak rate was slightly greater than the cover 602, averaged about 33 ccm, and the leak rate was maintained for greater than 120 minutes.

Each of the cover 601, the cover 602, and the cover 603, was constructed without a scrim layer. The cover 601, the cover 602, and the cover 603 each exhibited the ability to provide a good seal over a tissue site. Consequently, the construction of the cover 601, the cover 602, and the cover 603, having a film layer, a first adhesive layer, a third adhesive layer, a support layer, and a second adhesive layer, produces a cover suitable for use with negative-pressure therapy while increasing the ability to monitor a tissue site visually without having to remove the cover.

Figure 17:
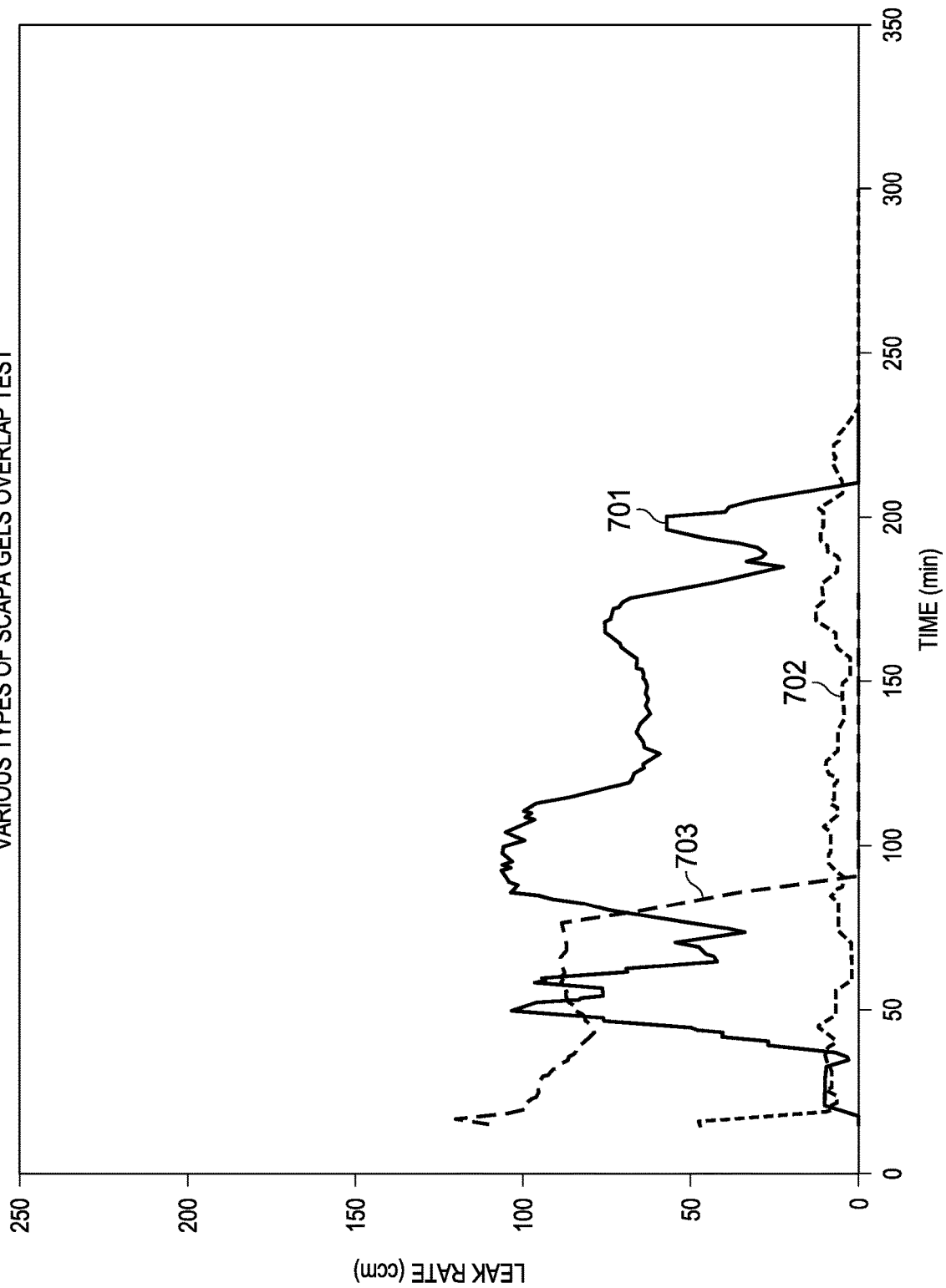
FIG. 17 is another graph of leak rate versus time for various covers, including the cover of FIG. 11.

FIG. 17 is a graphical depiction of leak rates for exemplary covers, illustrating additional details that may be associated with some embodiments. In the example, each cover was positioned on a testing apparatus having a grid of channels formed therein. The channels of the grid had a depth of approximately 150 microns, and each channel was spaced approximately 0.75 mm from adjacent channels. The cover was placed over the grid, and sealed to the surface of the grid. A secondary cover having an identical configuration was then placed over edges of the underlying cover. A negative-pressure therapy apparatus was fluidly coupled to an area between the cover and the grid, and negative-pressure therapy was conducted. During the test, a negative pressure of about 125 mmHg was maintained in the area between the cover and the grid. A leak rate of the covers was then calculated. The leak rate was determined based on the operation of the negative-pressure therapy apparatus to maintain the area under the exemplary covers at approximately 125 mmHg negative pressure. For example, the operation of the negative-pressure therapy apparatus was monitored. Based on a known flow rate for the negative-pressure therapy apparatus, the operational time of the negative-pressure therapy apparatus was measured to determine a total volume of fluid moved by the negative-pressure therapy apparatus during the operational time. From the total volume of fluid moved by the negative-pressure therapy apparatus for the operational time, the leak rate was calculated.

A first cover 701 was tested as described above to determine its leak rate. The cover 701 is similar to and includes the components of the cover 406. For the cover 701, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having a thickness of about 40 microns. The second adhesive layer 412 was formed from a silicone gel, such as a 6054 silicone gel produced by Scapa™, having a coating weight of about 150 gsm. The third adhesive layer was formed from an acrylic adhesive having a coating weight of about 20 gsm. As shown in FIG. 17, the cover 701 exhibited an increasing leak rate over time. The initial leak rate was about 0 ccm, and the leak rate varied over time from 0 minutes to approximately 200 minutes having a maximum leak of about 110 ccm.

A cover 702 was also tested as described above to determine its leak rate. The cover 702 is similar to and includes the components of the cover 406. For the cover 702, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having a thickness of about 25 microns. The second adhesive layer 412 comprised a silicone gel, such as a RX1423s silicone gel produced by Scapa™, having a coating weight of about 150 gsm. The third adhesive layer comprises an acrylic adhesive having a coating weight of about 20 gsm. As shown in FIG. 17, the cover 702 maintained a low leak rate over time. The initial leak rate was slightly greater than 0 ccm, and the leak rate was maintained within a range between about 0 ccm and about 10 ccm for about 200 minutes.

A cover 703 was also tested as described above to determine its leak rate. The cover 703 is similar to and includes components of the cover 406 as described above; however, the cover 703 did not include the third adhesive layer 413. In the example, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having thickness of about 25 microns. The second adhesive layer 412 was formed from a polyurethane gel, such as a 9772B polyurethane gel having a coating weight of about 200 gsm. As shown in FIG. 17, the cover 703 maintained a high leak rate between about 0 minutes and about 90 minutes. The leak rate substantially decreased to about 0 ccm as time approached 200 minutes.

Each of the cover 701, the cover 702, and the cover 703, was constructed without a scrim layer. The cover 701, the cover 702, and the cover 703 each exhibited the ability to provide a good seal over a tissue site. Consequently, the construction of the cover 701, the cover 702, and the cover 703, having a film layer, a first adhesive layer, a third adhesive layer, a support layer, and a second adhesive layer, produces a cover suitable for use with negative-pressure therapy while increasing the ability to monitor a tissue site visually without having to remove the cover.

Figure 18:
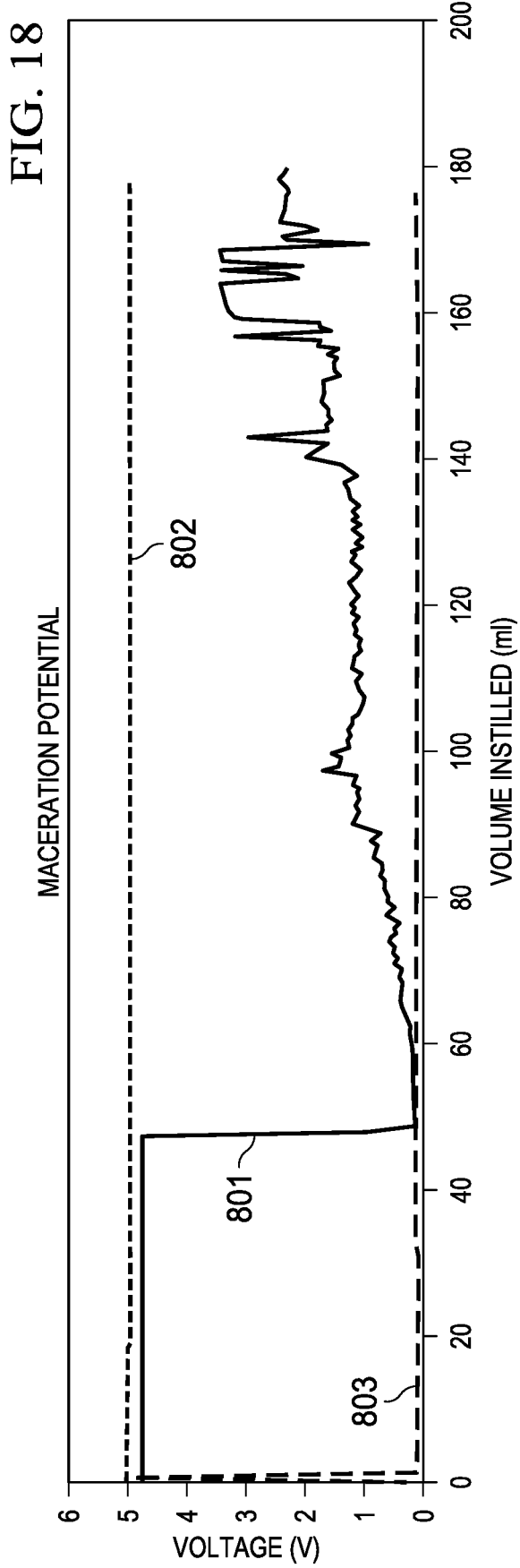
FIG. 18 is a graph depicting maceration tendency versus volume of fluid instilled in a tissue site sealed with the cover of FIG. 11.

FIG. 18 is a graphical depiction of maceration potential for exemplary covers, illustrating additional details that may be associated with some embodiments. Maceration may refer to the breakdown of skin tissue after prolonged exposure to moisture. In the example, covers were tested to determine each cover's potential to encourage or hinder maceration of healthy tissue. The test apparatus included a substantially smooth surface having electrodes positioned at intervals on the surface. Each cover was placed over the electrodes and sealed to the smooth surface. In the example embodiment, a tissue interface was also placed on the surface, and the cover was sealed to the surface around the tissue interface. Fluid was circulated to the tissue interface to simulate an instillation therapy. In the example embodiment, approximately 180 ml of fluid was instilled into the tissue interface. A current was applied to the electrodes, and the resulting voltage was measured across the electrodes as the fluid is instilled into the tissue interface. If fluid seeps between the cover and the surface surrounding the tissue interface, the resistance between the electrodes can change, indicating the presence of fluid and the potential for maceration. A higher voltage measurement indicates that the moisture content between the surface and the cover is low and, consequently, indicates a lower potential for maceration of the tissue surrounding the tissue site. A lower voltage measurement indicates that the moisture content between the surface and the cover is high and, consequently, indicates a higher potential for maceration of the tissue surrounding the tissue site.

A first cover 801 was tested as described above to determine its maceration potential. The cover 801 is similar to and includes the components of the cover 406 as described above. For the cover 801, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having a thickness of about 40 microns. The second adhesive layer 412 was formed from a silicone gel, such as a 6054 silicone gel produced by Scapa™, having a coating weight of about 150 gsm. The third adhesive layer was formed from an acrylic adhesive having a coating weight of about 20 gsm. As shown in FIG. 18, the cover 801 maintained a voltage measurement of slightly less than 5 volts through approximately 50 ml instilled. Across the first 50 ml instilled, the cover 801 exhibited low maceration potential. At approximately 50 ml, the voltage measured began to varying indicating that as additional fluid was instilled, the potential for maceration increased.

A cover 802 was also tested as described above to determine its maceration potential. The cover 802 is similar to and includes the components of the cover 406 as described above. For the cover 802, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having a thickness of about 25 microns. The second adhesive layer 412 comprised a silicone gel, such as a RX1423s silicone gel produced by Scapa™, having a coating weight of about 150 gsm. The third adhesive layer comprises an acrylic adhesive having a coating weight of about 20 gsm. As shown in FIG. 18, the cover 802 maintained a voltage measurement of about 5 volts through approximately 180 ml instilled, indicating that the potential for maceration is minimal.

A cover 803 was also tested as described above to determine its maceration potential. The cover 803 is similar to and includes components of the cover 406 as described above; however, the cover 803 did not include the third adhesive layer 413. In the example, the film layer 414 was formed from a polyurethane film having a thickness of about 30 microns, and the first adhesive layer 410 was formed from an acrylic adhesive having a coating weight of about 45 gsm. The support layer 411 was formed from a polyurethane film having thickness of about 25 microns. The second adhesive layer 412 was formed from a polyurethane gel, such as a 9772B polyurethane gel having a coating weight of about 200 gsm. As shown in FIG. 18, the cover 803 the voltage measurement immediately dropped to approximately 0 volts as fluid began to be instilled. The cover 803 maintained the voltage measurement through approximately 180 ml instilled, indicating a high risk for potential maceration.

Each of the cover 801, the cover 802, and the cover 803, was constructed without a scrim layer. The cover 801, the cover 802, and the cover 803 each exhibited the ability to provide inhibit maceration of tissue adjacent a tissue site. Consequently, the construction of the cover 801, the cover 802, and the cover 803, having a film layer, a first adhesive layer, a third adhesive layer, a support layer, and a second adhesive layer, produces a cover suitable for use with negative-pressure therapy while increasing the ability to monitor a tissue site visually without having to remove the cover.

The manufacturing processes described herein can produce a cover without the use of a scrim layer. Typically, a scrim layer is needed to provide support for the cover 106, the cover 206, the cover 306, and the cover 406 during the manufacturing process. By manufacturing the cover 106, the cover 206, the cover 306, and the cover 406 without a scrim layer, the light transmittance of the final product can be increased while providing additional support to the cover 106, the cover 206, the cover 306, and the cover 406, for example, in embodiments having the support layer 111 disposed between the first adhesive layer 110 and the second adhesive layer 112. Furthermore, the cover 106, the cover 206, the cover 306, and the cover 406 may have improved clarity aiding more accurate cover positioning and visualization of the wound filler and periwound, increased flexibility and conformability, more efficient use of the adhesives, which enable a thinner coating of adhesive, and reduced manufacturing costs. Still further the cover 306 may accommodate shrinkage between the various materials forming the cover 306.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations a dressing, a container, or both may be eliminated or separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A tissue cover including a first film layer having a first side and a second side, a first adhesive layer coupled to the first film layer, and a second adhesive layer coupled to the first adhesive, the second adhesive layer having a plurality of perforations extending through the second adhesive layer, the first film layer, the first adhesive layer, and the second adhesive layer being coextensive, the cover formed by a process comprising the steps of:

coupling a first adhesive to the second side of the first film layer to form the first adhesive layer having a first side adjacent to the second side of the first film layer;

coupling a second adhesive to a second film layer to form the second adhesive layer having a first side adjacent to the second film layer;

forming one or more perforations through the second film layer and the second adhesive layer;

coupling a second side of the second adhesive layer to a second side of the first adhesive layer; and removing the second film layer.

2. The tissue cover of claim 1, wherein coupling the first adhesive to the second side of the first film layer comprises casting the first adhesive onto the first film layer.

3. The tissue cover of claim 1, wherein coupling the first adhesive to the second side of the first film layer comprises laminating the first film layer to the first adhesive.

4. The tissue cover of claim 1, wherein coupling the first adhesive to the second side of the first film layer further comprises curing the first adhesive.

5. The tissue cover of claim 1, wherein forming one or more perforations through the second film layer and the second adhesive layer comprises punching one or more perforations through the second film layer and the second adhesive layer.

6. The tissue cover of claim 1, wherein forming one or more perforations through the second film layer and the second adhesive layer comprises cutting one or more perforations through the second film layer and the second adhesive layer.

7. The tissue cover of claim 1, wherein forming one or more perforations through the second film layer and the second adhesive layer comprises melting one or more perforations through the second film layer and the second adhesive layer.

8. The tissue cover of claim 1, wherein forming one or more perforations through the second film layer and the second adhesive layer comprises drilling one or more perforations through the second film layer and the second adhesive layer with a rotary tool.

9. The tissue cover of claim 1, wherein forming one or more perforations through the second film layer and the second adhesive layer comprises forming each perforation with an average effective diameter between about 2 mm and about 50 mm.

10. The tissue cover of claim 1, wherein forming one or more perforations through the second film layer and the second adhesive layer comprises forming each perforation with an average effective diameter of about 30 mm.

11. The tissue cover of claim 1, wherein forming one or more perforations through the second film layer and the second adhesive layer comprises forming each perforation with an average effective diameter of about 7 mm.

12. The tissue cover of claim 1, wherein forming one or more perforations through the second film layer and the second adhesive layer comprises forming one or more perforations so that adjacent perforations have centers separated by between about 5 mm and about 100 mm.

13. The tissue cover of claim 1, wherein forming one or more perforations through the second film layer and the second adhesive layer comprises forming one or more perforations so that adjacent perforations have centers separated by about 10 mm.

14. The tissue cover of claim 1, wherein forming one or more perforations through the second film layer and the second adhesive layer comprises removing about 50% of a surface area of the second film layer and the second adhesive layer.

15. The tissue cover of claim 1, wherein the second adhesive comprises a silicone gel.

16. The tissue cover of claim 15, wherein the silicone gel is a two-part silicone system and the process further comprises:
providing a first part of the two-part silicone system;
providing a second part of the two-part silicone system;
mixing the first part with the second part to form a two-part silicone gel; and
curing the two-part silicone gel.

17. The tissue cover of claim 15, wherein the silicone gel is a one-part silicone.

18. The tissue cover of claim 1, wherein coupling the first side of the second film layer to the second side of the first adhesive layer comprises laminating the first side of the second film layer to the second side of the first adhesive layer.

19. The tissue cover of claim 1, wherein coupling the second adhesive to the second film layer is performed without use of a scrim layer.

20. The tissue cover of claim 1, wherein coupling the first adhesive to the first film layer is performed without use of a scrim layer.

21. The tissue cover of claim 1, wherein:
coupling the first adhesive to the first film layer is performed without use of a scrim layer; and
coupling the second adhesive to the second film layer is performed without use of a scrim layer.

22. The tissue cover of claim 1, wherein the second adhesive layer has a coating weight between about 150 gsm and 250 gsm.

23. The tissue cover of claim 1, wherein the first adhesive layer has a coating weight between about 10 gsm and about 60 gsm.

24. The tissue cover of claim 1, wherein the second adhesive further comprises a platinum catalyst.

25. The tissue cover of claim 1, wherein the second adhesive further comprises a sulfur catalyst.

26. The tissue cover of claim 1, further comprising forming a sizing line through the combined first film layer, the first adhesive layer, and the second film layer.

27. The tissue cover of claim 26, wherein the sizing line comprises a plurality of sizing lines equidistantly spaced from each other across the tissue cover.

28. The tissue cover of claim 26, wherein forming the sizing line comprises forming a plurality of perforations through the first film layer, the first adhesive layer, and the second film layer.

29. The tissue cover of claim 28, wherein the perforations comprise slits spaced about 25 mm to about 60 mm from adjacent slits.

30. The tissue cover of claim 28, wherein the plurality of sizing lines are between about 5 cm and about 30 cm from adjacent sizing lines.

31. The tissue cover of claim 28, wherein the plurality of sizing lines are about 18 cm from adjacent sizing lines.

32. The tissue cover of claim 1, wherein a transmittance of the cover is between about 70% and about 100%.

33. The tissue cover of claim 1, wherein a transmittance of the cover is about 90%.

34. The tissue cover of claim 1, wherein a color perceived through the cover is substantially the same as the color perceived independently of the cover.

35. The tissue cover of claim 1, wherein the process further comprises the step of removing the second film layer.

* * * * *